(12) United States Patent
Simmons

(10) Patent No.: US 10,165,940 B2
(45) Date of Patent: *Jan. 1, 2019

(54) VISION-BASED DIAGNOSIS AND TREATMENT

(71) Applicant: John C Simmons, Germantown, TN (US)

(72) Inventor: John C Simmons, Germantown, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/291,056

(22) Filed: Oct. 11, 2016

(65) Prior Publication Data

US 2017/0027805 A1   Feb. 2, 2017

Related U.S. Application Data

(63) Continuation of application No. 14/215,167, filed on Mar. 17, 2014, now Pat. No. 9,463,132.

(60) Provisional application No. 61/800,511, filed on Mar. 15, 2013.

(51) Int. Cl.

| A61H 5/00 | (2006.01) |
|---|---|
| A61B 3/113 | (2006.01) |
| A61B 3/00 | (2006.01) |
| A61B 5/16 | (2006.01) |
| A61B 5/00 | (2006.01) |
| A61B 3/08 | (2006.01) |
| G16H 50/30 | (2018.01) |
| G16H 50/20 | (2018.01) |
| G06F 19/00 | (2018.01) |
| A61B 3/14 | (2006.01) |

(52) U.S. Cl.
CPC .......... *A61B 3/085* (2013.01); *A61B 3/0025* (2013.01); *A61B 3/0058* (2013.01); *A61B 3/113* (2013.01); *A61B 3/145* (2013.01); *A61B 5/16* (2013.01); *A61B 5/165* (2013.01); *A61B 5/168* (2013.01); *A61B 5/4836* (2013.01); *A61B 5/7282* (2013.01); *A61B 5/741* (2013.01); *A61H 5/005* (2013.01); *G06F 19/00* (2013.01); *G06F 19/3481* (2013.01); *G16H 50/20* (2018.01); *G16H 50/30* (2018.01); *A61H 2201/1604* (2013.01); *A61H 2201/165* (2013.01); *A61H 2201/5007* (2013.01); *A61H 2201/5043* (2013.01); *A61H 2201/5092* (2013.01)

(58) Field of Classification Search
CPC .......... A61B 3/08; A61B 3/085; A61B 3/113; A61B 5/16; A61B 5/165; A61B 5/168; A61B 5/4836; A61B 5/7283; A61B 5/741; A61B 3/005; A61B 3/0058; A61B 3/0066; A61B 3/0075; A61H 5/005
USPC .......................... 351/201–203, 246; 600/558
See application file for complete search history.

(56) References Cited

U.S. PATENT DOCUMENTS

2013/0321772 A1*  12/2013  White .................... A61B 3/113
                                                    351/209

* cited by examiner

*Primary Examiner* — Marin Pichler

(57) ABSTRACT

Devices and methods are provided herein for aiding in the diagnosis of and response to conditions ranging from unpleasant to disabling. Images are presented to viewers and eye-tracking of their eyes during that process along with software analysis non-subjectively identify and quantify complex visual signatures formerly hidden in the responses of the eyes. This allows caregivers, when presenting these images to people to be evaluated for a condition, to identify, again with eye-tracking and software analysis, those signatures indicative of a presence or an absence of the condition. An associated remediative response provides treatment applicable to a real-time environment.

14 Claims, 18 Drawing Sheets

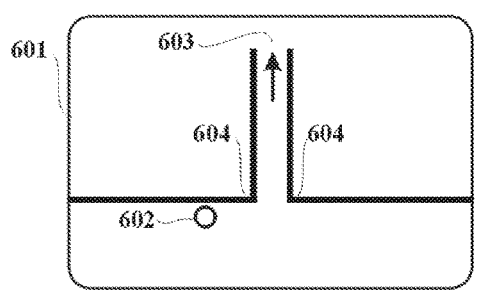 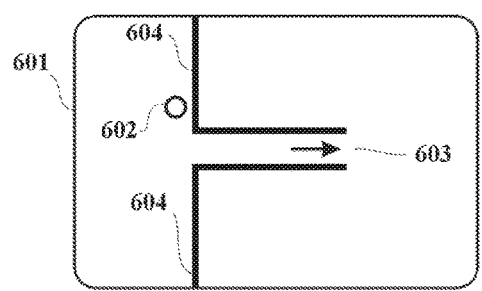
Fig. 6A                              Fig. 6B

ScoringPrimary
Primary Database Table:
FrameNumber:        21
VideoReference:     0

Child Database Table: ScoringChild
FrameNumber             21
VignetteNumber          1
MeaningAttribute        11
TargetCoordinates       0074300216
TargetStrikeValue       -41
TargetFullValueRadius   27
TargetFullValueWidth    0
TargetFullValueHeight   0
TargetFullValueEllipseA 0
SpatiallyDeprRespCurve  3
SpatiallyDeprRespRange  75
TimeFactor (Integer).   5
ScoreThresholdPositive  2
ScoreThresholdNegative  -2
SkipFrames              0
Condition               0
AnchorPower             0

Fig. 7A

Primary Database Table: ScoringPrimary
FrameNumber:        22
VideoReference:     0

Child Database Table: ScoringChild
FrameNumber             22
VignetteNumber          1
MeaningAttribute        25
TargetCoordinates       0075100208
TargetStrikeValue       -41
TargetFullValueRadius   27
TargetFullValueWidth    0
TargetFullValueHeight   0
TargetFullValueEllipseA 0
SpatiallyDeprRespCurve  3
SpatiallyDeprRespRange  75
TimeFactor              5
ScoreThresholdPositive  2
ScoreThresholdNegative  -2
SkipFrames              0
Condition               0
skip frames             0
Condition               0
AnchorPower             0

Fig. 7B

Primary Database Table: ScoringPrimary
FrameNumber:      22
Video reference:  0

Child Database Table: ScoringChild
FrameNumber            22
VignetteNumber         2
MeaningAttribute       25
TargetCoordinates      0019300437
TargetStrikeValue      +38
TargetFullValueRadius  125
TargetFullValueWidth   0
TargetFullValueHeight  0
TargetFullValueEllipseA 0
SpatiallyDeprRespCurve  3
SpatiallydeprRespRange  50
TimeFactor             5

ScoreThresholdPositive  2
ScoreThresholdNegative -2
SkipFrames              0
Condition               0
AnchorPower             0

Fig. 7C

Step one Parent table: (indexed by subject condition)
  SubjectNumber (Integer)
  SubjectCondition (Integer) (e.g.,1 for healthy)

Child table: (indexed by subject number + frame number)
  SubjectNumber (Integer)
  FrameNumber (Integer) and
  TargetCoordinates (String, 10)

Fig. 7D

```
Program ScoreVictims(Frame,Adv);Run scoring to see if this pass on grand tour is good.
select OptimizationDataFBF: If Adv=0 then append blank
select ScoringChild; Now we open the file of anchors just created&score against POI's
set index to AnchorScoring: E=0
do case
   case Adv=0: PO=0:AR=0; $1^{st}$ pass to score POI's vs. anchors for their own cond code
   case Adv=1: PO=1:AR=-1;$1^{st}$ recursive pass ($2^{nd}$ pass) POI's for cond x vs. cond for x-1
   case Adv=2: PO=0:AR=1;E=1;$2^{nd}$ recurs. POI's for cond x scored to anchors for x+1
endcase
;For each arrayPOI condition(),frame()&POI()consider all anchors in frame&sum score
For Cond = (1+PO) to (4-E)
   Scor=0
   If Cond = 1 ; go thru POI array from top... condition(), frame(), and POI()
      a=1: b= NumCondition(1); in this example, 1 – 100 of healthy responses
   else
      a=1+NumCondition(Cond-1): b=NumCondition(Cond())
   end    ; v— i below counts thru POI's in unbroken sequence
      ;         v--- for each POI array record, apply all applicable anchors
   for i = a to b ; e.g., for cond=1:  1 to 100 POI recs in ex. w/100 condition 1 subjects
      xx=val(left(POI(i),5));  ; get $1^{st}$ POI coordinates from array
      yy=val(right(POI(i),5))
      select ScoringChild
      success=seek(padl(str(Frame),5,"0") + padl(str(Cond+AR),5,"0")
      ; Came w/1POI applic.to 1 cond. Score it to ALL scoring anchors for frame&cond...
      do while (FrameNumber=Frame) and (Cond+AR=Condition) and not (eof)
         ; SCORING
         x=val(left(TargetCoordiantes,5)); y=val(right(TargetCoordinates,5))
         Dist=FindDistRad(x,y,xx,yy); find distance from POI to target coord for this anchor
         do case
           case TargetFullValueRadius>=Dist
              Scor=Scor+TargetStrikeValue
           case abs(Dist-TargetFullValueRadius) <=SpatiallyDeprRespRange
              T=TargetStrikeValue: TR=TargetFullValueRadius
              SC=SpatiallyDeprRespCurve:SR=SpatiallyDeprRespRange
              Scor=Scor+ GetSpatDeprCurve(T,Dist,SC,SR,TR)
         endcase
         skip; advance to next record
      enddo
   endfor ; next array--^   or thru w/all array POI's for instant cond---v
```

Fig. 10A

```
                              ; Finished all scoring for this cond, now remember it...
   Scor=Scor/(b-a+1) ;  make Scor an avg score for all POI's in this condition class
   select OptimizationDataFBF
   do case
      case Cond=1 and Adv=0: repl Cond1AvgScore with Scor ; 1st pass we simply get scor
      case Cond=2 and Adv=0: repl Cond2AvgScore with Scor ; for POI's against anchors
      case Cond=3 and Adv=0: repl Cond3AvgScore with Scor ; for their own Cond. Next
      case Cond=4 and Adv=0: repl Cond4AvgScore with Scor ; we get #2POI's vs.#1Cond case Cond=2 and Adv=1: repl Cond2Pto1A with Scor ; Cond2 POI→Cond1 Anchors
      case Cond=3 and Adv=1: repl Cond3Pto2A with Scor ; Cond3 POI→Cond2 Anchors
      case Cond=4 and Adv=1: repl Cond4Pto3A with Scor ; Cond4 POI→Cond3 Anchors case Cond=1 and Adv=2: repl Cond1Pto2A with Scor ; Cond1 POI→Cond2 Anchors
      case Cond=2 and Adv=2: repl Cond2Pto3A with Scor ; Cond2 POI→Cond3 Anchors
      case Cond=3 and Adv=2: repl Cond3Pto4A with Scor ; Cond3 POI→Cond4 Anchors
   endcase
end    ; next cond....

Do case ;  Finished all scoring for all 4 conds. Now recursively recall to compare left/right
   case Adv=0: 1st pass got POI's against all their condition anchors:Recursively call now...
      call ScoreVictims(Frame,1); Recursively call this program with Adv=1
   case Adv=1: 2nd pass done. Now recursively call w/ Adv=2
      call ScoreVictims(Frame,2); Recursively call this program with Adv=2
   case Adv=2;If this is the 3rd (last) pass thru this recursively called prog→grade params
      MinRatio1=1.5:MinRatio2=1.35:MinRatio3=1.35 ; MinRatio4=1.2; exemplary:
      ;implementer selected.
      ;The higher the ratio of POI's scored against their own condition's anchor values to the
      ; next group, the better the wall of separation between them
      Rat=0 ; These rating algorithms will be modified by implementers:10 points=best score
      if abs(Cond1AvgScore/Cond2Pto1A) >MinRatio1 then Rat=Rat +1;cond-shift separatn
      if Cond2AvgScore/Cond3Pto2A >MinRatio2 then Rat=Rat +1
      if Cond3AvgScore/Cond4Pto3A >MinRatio2 then Rat=Rat +1
      if Cond4AvgScore/Cond4Pto3A >MinRatio3 then Rat=Rat +1
```

Fig. 10B

```
    if abs(Cond2AvgScore/Cond1Pto2A) >MinRatio1 then Rat=Rat +1;cond+shift sep.
    if Cond3AvgScore/Cond2Pto3A >MinRatio2 then Rat=Rat +1;cond+shift separation
    if Cond4AvgScore/Cond1Pto2A >MinRatio1 then Rat=Rat +1;cond+shift separation if abs(Cond2AvgScore/Cond1AvgScore)>MinRatio4 then Rat=Rat+1;  Cond separation
    if Cond3AvgScore/Cond2AvgScore>MinRatio4 then Rat=Rat+1;       Cond separation
    if Cond4AvgScore/Cond3AvgScore>MinRatio4 then Rat=Rat+1;       Cond separation
    repl ODefRange1 with DefRange1: repl ODefRange2 with DefRange2 ; save the opti-
    repl ODefRange3 with DefRange3: repl OMinHits with MinHits;    -mization criteria
    repl Score with Rat; This field, when sorted, lists criteria in order of effectiveness
endcase
Return Function GetSpatDeprCurve(T,Dist,SC,SR,TR)
        ; T=TargetStrikeValue: TR=TargetFullValueRadius
        ; SC=SpatiallyDeprRespCurve:SR=SpatiallyDeprRespRange
    ; exemplary curve #SC is a depreciating val from T to 0 over the course of SR
    ; simple ramp here but alternatives include Gaussian curve based on FWHM@TR, etc.
    Return (-1)*(abs(T)/SR)* (abs(Dist-TR)) +T
```

Fig. 10C

We come to these programs with the captured POI arrays from previous steps open and active.
These are condition(), frame(), and POI() and they are still in order of frame+condition ; Set Globals
Close all: Clear all:Public DefRange1:Public DefRange2:Public DefRange3:
Public XRange:Public YRange:XRange=1024:YRange=768; chosen by implementers
Public NumCondition(); Public MinHits:
Public Hit1Weight:Public Hit2Weight: Public Hit3Weight
Hit1Weight=1: Hit2Weight=1:Hit3Weight = 1; may also be optimize vals or by implemntr
Dimension NumCondition(4):
Public ThresholdWeight: ThresholdWeight=0.5; may be optimize values
NumCondition(1)=100:NumCondition(2) =121; $2^{rd}$ group from 101 to 121, etc.
NumCondition(3)=202 :NumCondition(4)=300: NumFrames= 9000; 5 min @30fps open database ScoringChild ; Database of Fig. 7A created earlier and empty
index on padl(str(FrameNumber),5,"0") + padl(str(Condition),5,"0") to AnchorScoring ' Create empty SPT table for optimization data
create table OptimizationDataFBF ; Optional Optimization for each frame or 1 for all
   OFrame, i ;
   ODefRange1, i ;
   ODefRange2, i ;
   ODefRange3, i ;
   OMinHits, i;
   Cond1AvgScore N(10,2) ; using Cond1 POI's
   Cond2AvgScore N(10,2) ;
   Cond3AvgScore N(10,2) ;
   Cond4AvgScore N(10,2)
   Cond2Pto1A   N(10,2) ; Used to capture Cond2 POI's vs. Cond1 scoring templates
   Cond3Pto2A   N(10,2) ; etc, to expose any failures to differentiate the group's
   Cond4Pto3A   N(10,2)
   Cond1Pto2A   N(10,2)
   Cond2Pto3A   N(10,2)
   Cond3Pto4A   N(10,2)
   Score          N(10,2); 10 is highest relevance score
Call GrandTour()

Fig. 11

```
Program GrandTour() ;          using partial list of parameters ranges
For Frame = 1 to NumFrames ; implementers will adjust ranges for D1,D2,M, etc.
   for D1= 12 to 35 ;  Discover POI clusters responsive to a condition and optimize
      DefRange1 = D1 ;  spatial range sensitivity beyond TargetFullValueRadius
      for D2=45 to 70
         DefRange2=D2 ; spatial range of SpatiallyDeprRespRang
         for D3=80 to 120
            DefRange3=D3
            for M=55 to 80
               MinHits=M;
               Call MakeAnchors(Frame);(PCR)+Anchors for each density point, all cond's
               call ScoreVictims(Frame,0) ; Run scor prog&validate pass on grand tour
            end
         end
      end
   end
ends
select OptimizationDataFBF:Index on score descending to Optimized:Go top
List fields ODefRange1, ODefRange2, ODefrange3,OMinHits; View optimized criteria.
Program MakeAnchors(Frame) ;Make Anchors for each screen density point,all cond's.
Select ScoringChild:  Zap ;  Open and delete any records for child database of Fig. 7A
for ConditionCode = 1 to 4;  i.e. from healthy (1) to severe (4)
   for y = 1 to yrange;   start considering each pixel as a possible cluster center at 1,1
      for x=1 to xrange
         p=TempScoreRecs(ConditionCode),x,y,f) ;+anchor if enough POI's here
      end
   end
end
```

Fig. 12A

```
function TempScoreRecs(CondNum,x,y,f); For x,y,Scan POI's & + Anchors
Hits1=0:Hits2=0:Hits3=0 ; counter _
If CondNum = 1
   a=1: b=NumCondition(1); in this example, 1 – 100 of healthy responses
else
   a=1+NumCondition(CondNum-1): b=NumCond(Condnum)
end    ; v— i below counts thru POI's in unbroken sequence ; For this x,y, go thru all POI's for instant frame&condit& save if x,y is an anchor
for i = a to b ; e.g., for cond=1:  1 to 100 POI recs in ex. w/100 condition 1 subjects
   xx=val(left(POI(i),5));  ; get 1st POI coordinates from array
   yy=val(right(POI(i),5))
   Distance = FindDistRad(x,y,xx,yy) ;   find distance between x,y point on screen & POI
   Do case
      Case abs(DefRange1 – Distance) >= 0
         Hits1=Hits1 + 1
      Case abs(DefRange2 – Distance) >= 0
         Hits2=Hits2 + 1
      Case abs(DefRange3 – Distance) >= 0
         Hits3=Hits3 + 1
   endcase
end
SortVal = Hits1*Hit1Weight+Hits2*Hit2Weight +Hits3*Hit3Weight
If SortVal>MinHits ; MAKE ANCHOR:don't waste proc. time on non-dense anchors
   Select ScoringChild; select already score table to save scoring for x,y as density anchor
   Append blank ; create an empty database record (arrays optional)
   replace FrameNumber with f
   replace VignetteNumber with 0; added later by implementers
   replace TargetCoordinates with padl(str(x),5,"0")+ padl(str(y),5,"0")
   signn=1:if CondFigure hen signn=-1; sign for next line
   replace TargetStrikeValue with signn*Hit1Weight*Hits1
   replace TargetFullValueRadius with DefRange1; R that the point of focus 107 can be far
beyond the screen 102.
ect.&ellipse methods not shown here
   replace SpatiallyDeprRespCurve with 1; exemplary curve #1 shown in GetSpatDeprCurve
   replace SpatiallyDeprRespRange with DefRange2
   replace TimeFactor with zero; not used in this example
   replace ScoreThresholdPositive with Hits1 * ThresholdWeight
   replace ScoreThreshold negative with Hits1 * ThresholdWeight; implementer adj
   replace skip frames with 0; may be changed by optimizer or implementer
   replace condition with CondNum
   replace Anchorpower with SortVal
Return SortVal
```

Fig. 12B

Function FindDistRad(x,y,xx,yy); Radius-based dist. Rectangular&Ellipse
  ; numerous other spatial area recognitions options are applicable and locatable here
  return ((xx-x)^2+(yy-y)^2)^0.5

Fig. 12C

VISION-BASED DIAGNOSIS AND TREATMENT

This application claims the benefit of the provisional application U.S. Ser. No. 61/800,511 filed Mar. 15, 2013. That application is entitled "Vision-Based Diagnosis and Treatment."

This application also claims the benefit of the subsequent utility patent application U.S. Ser. No. 14/215,167 filed on Mar. 17, 2014. That application is also entitled "Vision-Based Diagnosis and Treatment."

Both of these applications are referred to and incorporated herein by reference in their entirety.

BACKGROUND OF THE INVENTION

Strabismus, sometimes referred to as "lazy eye," is a medical condition of the eye normally treated by disabling or otherwise interfering with the vision of the strong eye so that the patient will be forced to use the "lazy" one. Although the current treatments for Strabismus (chemically paralyzing, numbing or blocking the strong eye with an opaque patch) are unpleasant and, consequentially, irregularly applied, they can be effective if they are used consistently. Their effectiveness as a normative treatment for Strabismus appears to be related to the brain's ability, under external duress, to recognize and correct certain factors that result in poor vision.

Autism, a pervasive developmental disorder recognizable by physical rigidity, emotional detachment and impaired communication is both a major and a growing threat to children. According to a study published in *Pediatrics*, Oct. 5, 2009, based on a National Children's Health Survey done with 78,000 parents in 2007, 1 percent of the population of children in the U.S. ages 3-17 have an autism spectrum disorder. It is also the fastest growing developmental disability (10-17% annual growth) according to an Autism Society estimate based on 2003 US state educational data.

Both disorders are especially prevalent in children, desperately need early diagnosis for a successful outcome and share a dearth of effective treatments whose side effects, discomfort, tedium and cosmetic disincentives to compliance do not require more patience and social confidence than this young and already emotionally challenged population can live up to.

Eye-tracking is a broadly used technology to determine the vision axes of the eyes. Then, responsive to their position and orientation, it can be determined essentially where the subject is looking. There are a wide variety of technologies for tracking the vision axis of each eye, all of which are applicable to the current invention.

For example, Mason in U.S. Pat. No. 3,462,604 on Aug. 19, 1969 uses an oculometer (a device that records the differences in electrical charge between the front and back of the eye. This can then be correlated with eyeball movement).

Graf in U.S. Pat. No. 4,109,145 issued Aug. 22, 1978 uses an oculometer or any other line of sight determining device and measures the length of static fixation. If the time of fixation passes a threshold value, the apparatus produces a control output (it's considered a valid fixation rather than an unintentional saccade).

U.S. Pat. No. 3,724,932 issued to Cornsweet et al. Apr. 3, 1973 uses a plurality of Purkinje images from the reflective surfaces of the eye. Monitoring the separation of the Purkinje images indicates the orientation of the optic axis of the eye.

U.S. Pat. No. 4,866,229 issued to Scharfenberg on Sep. 12, 1989 uses a heads-up display to track the eyes while the heads-up display is worn.

U.S. Pat. No. 4,651,145 issued to Sutter on Mar. 17, 1987 uses oculo-encephalographic signals captured responsive to unique coded signals presented to the subject with the EEG signal then used to determine where the subject is looking.

U.S. Pat. No. 5,293,187 uses electro-oculogram signals to control video devices.

Knapp et al. in U.S. Pat. No. 5,293,187, issued Mar. 8, 1994, which "relates generally to the operation of three-dimensional games and devices and strabismus measurement by determining the independent position of each eye" used an electrooculogram (electro-oculogram signals are, in effect, an electrical signature of eye movement that is not sensitive to ambient light interference) to determine eye position and to determine the horizontal and vertical position of each eye as well to determine convergence or divergence of the eyes. The signals representing eye position are interfaced to an output device for strabismus measurement. It is for diagnostic purposes only

BRIEF SUMMARY OF THE INVENTION

It is an object of the current invention to provide both a means for early diagnosis of autism and a means for its treatment that encourages remediation in even the youngest of patients.

It is another object of the current invention to provide a means for early diagnosis of strabismus and a means for its treatment that encourages remediation in even the youngest of patients.

Is another object of the current invention to provide a real-time response to recognized conditions that is both timely and graduated to enable minimally distraction and immediate patient comprehension of a need for correction, a recommended magnitude of correction and, where applicable, a recommended direction of correction.

It is another object of the current invention to be in an adequately comfortable and cosmetically acceptable form conducive to long-term application periods and patient compliance for these and other conditions recognizable by their ocular orientations and movements.

It is another object of the current invention to integrate other stimuli and recognized patient symptoms into an improved diagnosis and response that benefits from multiple presented indicia.

It is another object of the current invention to execute algorithms responsive to real-time data over time to identify trends and conditions and both alert and aid physicians in treatment and analysis as well as provoke remediative user response by one or a plurality of system responses.

It is another object of the current invention to self-generate a set of scoring criteria responsive both to the visual responses of viewers with known and well established levels of the condition in question and to age and other key indicator factors applicable to making the current invention more precisely tuned to specific patients. Thus the current invention is applicable to self-scoring for general research (applicable to discovering and scaling new vision indicators) and to a continually developing remediative program for any condition with predictable and normative visual responses.

BRIEF DESCRIPTION OF THE DRAWINGS

FIG. 6A and FIG. 6B illustrate the basis of another path-finding game.

FIG. 7A, FIG. 7B, FIG. 7C and FIG. 7D detail exemplary database structures useful to the discussion of one embodiment of the current invention.

FIG. 10A, FIG. 10B, FIG. 10C, FIG. 11, FIG. 12A, FIG. 12B and FIG. 12C list programmatic code related to scoring user responses and identifying parameters best suited to the purpose.

DETAILED DESCRIPTION OF THE INVENTION

Autism:

It is not the purpose of this description to describe or attempt to understand all the mysteries of autism many of which may continue to be mysteries for generations to come. Nor is it the intention of the current invention to solve all the problems associated with the widespread and rapidly advancing disorder. However, a number of ocular dynamics have been observed in the body of research to be normative of and often peculiar to those with autism. A few of the well known examples are that those with autism are highly prone to avoid eye contact (but able to look into the eyes of animals), fail to follow motive-interpreted actions and suggestions as well as to stray their instant point of interest (POI) to areas of no interest at all to other populations.

The POI can be any value relative to where the viewer is looking, e.g., along the cyclopic vision axis (and for some applications this won't even be on a screen) but, for a viewer looking at a screen, the POI can be thought of as the screen coordinates identified by the eye-tracking equipment for the point on the screen where the viewer is currently looking. (The cyclopic vision axis, a descriptive convenience, describes here an imaginary vision axis extending from the midpoint between the center of the two eyes, where the eye of the mythical Cyclops was, to the intersection point of the two vision axes when looking straight ahead. For example, when the viewer is looking straight ahead, the cyclopic axis follows the intersection of the sagittal plane and the particular transverse plane that intersects the center of the eyes thus forming an imaginary but useful descriptive device for identifying net singular direction of dual-eye subject fixation. When the subject looks away from dead center, the cyclopic axis rotates and continues to bisect the angle between the two real vision axes).

Because of the aforementioned difficulties of diagnosing autism as early as possible and providing extended treatment very early and for long periods to an extremely impatient demographic, the current invention provides a device and method for recognizing it at a very early age and with a statistically reliable diagnostic process and treating it with a user-friendly real-time responsive system.

Figure 1:
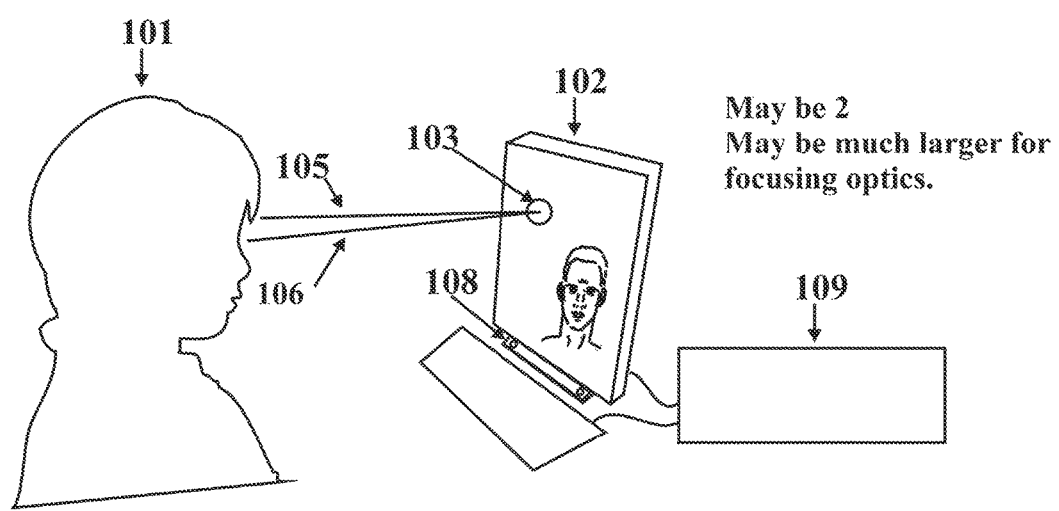
FIG. 1 illustrates a viewer, 101, observing a displayed image on a screen, 102, at a point 103. The images are being displayed by computer, 109 as the eyes of the observer are being tracked by the eye tracking assembly 108.

In one preferred embodiment, the subject, 101 in FIG. 1, looks at a video screen, 102. The source of the image on that screen can be from any source that can be associated with a set of values including network TV, cable, DVD, jump-drive, hard drive, streaming video, etc. However, in the embodiment shown, a personal computer, 109 provides a video image to the display, 102 from a video stored on a hard drive local to the computer, 109. An example session of one such embodiment is now explained essentially following part of the flow chart of FIG. 3.

The user interface, with user choices normally entered through the keyboard responsive to screen prompts, allows function selections, one of which is video selection. After any source and format of video is selected, the subject may choose to run the selected video (shown in the post video selection decision block of the flow chart in FIG. 3 as "Run Y/N"). If the selection is "Y", the program proceeds to begin loading the video and at least the first frame's (because each frame in a video is an independent image, a frame will sometimes be referred to herein as an image) corollary data. The paragraphs below are numbered with step labels identifying steps on the flow chart of FIG. 3.

A Loading Video and any Corollary Data:

Data identifying, for a short time period, scoring values for specific areas of the image, can be read from a storage device (e.g., a disc file) at the beginning of the process. For example, in step A of FIG. 3 all of the data for the entire video can be read into memory and used when needed. Or, of course, the data can also be accessed from the database table or other form of storage for each time period in the video as that time period comes up (this latter approach is the one described herein). It can even be stored in the video blanking interval of a television program. Any increment of time can be used to break the video down into convenient component parts. In the example embodiment being described here, frames are used as the minimum time segment. For example, if the video executes at 30 frames per second, each frame represents $\frac{1}{30}$ of a second. Multiple frames can then be grouped into vignettes of many contiguous frames which may be representative of a unique purposeful interlude and vignettes will often be scored independently to facilitate comparison of specific vignettes of activity between populations and known norms.

Then, as the prescreened video is being played, the thus retrieved scoring values for the instant frame are used to tabulate scores responsive to the importance (identified by the scoring values) of a POI occurring in prescribed areas.

More detail on what this involves is discussed further below. In this example embodiment, at minimum, the video file loading begins and at least the first frame is prepared for display. Thus, the software executing on the computer, 109, reads a video file from any storage device and displays at least the first frame on the display, 102. (Some alternative control software embodiments do not call or command individual video frames but otherwise synchronize scoring logic with the current frame being displayed and the current positions of the eyes. However, this example describes an embodiment that does.)

Also, corollary data, including data unique to the current frame of video, can now be retrieved from any storage means (a computer hard drive in the preferred embodiment).

Although the same corollary data can be used for both diagnosis and remediative treatment, they may also differ such as in level of calculation overhead required. For example, during a diagnosis cycle greater precision paid for by increased computer calculation overhead is practical even on a slow processor since the entire diagnosis can be processed on the back end as a batch process. However, real-time responsive remediative action and/or execution on a slow processor may result in slightly more time-efficient implementer choices for both corollary data values and procedures. Also, the corollary data examples shown below are merely exemplary of one of the many applicable embodiments of the current invention.

For example, corollary data (non-video image data) may include elements similar to or including the exemplary set in the data structure below.

Data Structure and Vignette Organization:

One of many applicable software application processes to manage this particular optional scoring technique is for implementers to first establish the range of frames that make up a vignette that may or may not be part of a considerably longer continuous presentation. In the preferred embodiment, the presentation is made up of a series of vignettes each with their own scoring attributes. In embodiments where this approach is used, the following data structure describes the general nature of a preferred format for a database stored on a computer hard-drive which may be loaded into memory prior to video viewing for faster access.

The primary database includes for each frame (although it is not a requirement, here we provide an individual database record for each frame) a value for at least frame number and vignette (frame-grouping) number. Although there can be multiple primary database records for a single frame, the preferred database structure makes that unnecessary as it is characterized by a one-to-many relationship between the primary database just described and a secondary database having one record for each cue rule for the frame that is represented by the instant single record of the primary database (here, using the frame number as the index key that relates the two tables). Here, the single primary database record for each frame can point to many records in a separate or corollary second table containing cue rules for the current record in the primary database (which refers to a single frame). In this preferred one-to-many relational database example, there is, of course, no need to store cue rules in the primary (first) database since they will be in the related secondary database. All alternative database approaches (e.g., SQL on-the-fly calls and pre-sequenced serial tables) are applicable to the current invention and obvious to those skilled in the art.

Example Primary Database Fields:

Parent (Primary) Table: ScoringPrimary

1. FrameNumber: (Integer) This is the number of the video frame this database record refers to. Where there is one primary database record for each video frame (this is the presumption for this example), this can optionally be replaced by the "record number" value maintained by many database engines. Alternatively, for slower processors or slow-action video segments requiring less time resolution, this frame number field may be used to represent a frame group number (for example one frame group number for every F frames). In that alternative case, complete processing would only be executed once for every F frames.

2. VideoReference: (Integer) This is a placeholder field representative of any related field data implementers use to provide information for and sync frame display with a given frame. While the current invention does not require any particular one of the various video control and synching methods (all are applicable), in an embodiment where a specific video frame is called for a given record in this database, this number may be used to identify that video data for display.

Of course, a third database related to the second could also be used for many of these values that are used many times (but is not in this exemplary description). For the related (secondary) database, we use here the corollary data fields already described above.

Child (Secondary) Table: ScoringChild

FrameNumber (Integer). This is the index key between the parent (primary) and child tables.

VignetteNumber (Integer). This identifies and groups a range of frames for which this particular meaning attribute (below) applies and will result in calculations for.

This number is also used to recognize the beginning and end of each vignette simply by when this number changes. Typically, scoring will be done at the vignette level and some or all of vignettes' data will be included in an overall summary report.

MeaningAttributes (Integer). This identifies the symptomatic characteristic whose tally will be affected by the score. (Note that a single meaning attribute can result in adjusting more than one tally). This can, of course, alternatively be a string value (rather than an integer) descriptive of a meaning which may be helpful in applications where there is a small number of meaning attributes. However, in the preferred embodiment the "handle" for a meaning attribute (such as "interpersonal eye engagement, opposite sex and adult") is a unique integer.

TargetCoordinates (String, 10). These values identify the location on the screen of a direct target "hit" for the meaning attribute for this child record. Example: "0012300777", in a 2-D implementation, represents the screen location 00123, 00777). These can be pixel numbers in a row and column format as is common or any other location identification strategy. Herein, the left set of values will be referred to as X (or column) values and right set as Y (or row) values. Target coordinates, as well as other field values below, may be entered by reviewer assistance software as described below.

TargetStrikeValue (Single Precision Decimal, 3). This is the base numerical scoring value for the viewer fixating precisely at the target coordinates. Admittedly, three decimal points seems excessive for the base calculation value for a "direct hit" within the target full value radius defined below. However, when the current invention's "Monte Carlo" process for scoring optimization is taken into account, this level of precision can, particularly in second and third levels of discretization processing, be of great value.

TargetFullValueRadius (Integer). This defines an optional tolerance circle for "full credit" of the target strike value. It indicates, how far away the POI can be from the target coordinates and still obtain the full target strike value score Actual distances between the POI and the target strike value will, of course, include non-integer values. For example, identifying left-right screen-location values as X values and up or down values as Y values, the distance to the target coordinates is calculated as:

$$D = ((X_t - X_p)^2 + (Y_t - Y_p)^2)^{1/2} \qquad \text{a.}$$

where Xt and Yt are target coordinates and Xp and Yp are POI coordinates. While this will certainly result in non-integer values, the level of precision required, particularly where location values are denominated by small pixels (for example where the target full value radius is expressed as a the number of pixel widths between POI and target coordinates), will normally be adequately met with an integer value for this field.

Additively or alternatively, the target full value radius can be augmented or replaced by target full value width and target full value height for similar operations using a rectangle centered at the target coordinates.

TargetFullValueWidth (Integer).

TargetFullValueHeight (Integer) Where rectangular (rather than circular as used in target full value radius) area containment for full value is desired, these width and height values provide the means to determine if the POI falls within one half of the width value to the left or right of the target coordinates and within one half of the height value above and below the target coordinates by simple subtraction of Cartesian coordinate values of the target coordinates and the POI as is widely understood.

TargetFullValueEllipseA (Integer) Where an elliptical area of containment is desired, it can be determined if the POI falls within an ellipse having a major axis twice the magnitude of the minor axis. Using X' as the absolute difference in x between the POI and the target coordinates and Y' as the absolute difference in y (vertical on the screen) between the POI in the target coordinates, the maximum value for the magnitude of the POI y coordinate is obtained using the equation:

$$Y=a/2*sqrt(1-(x^2/a^2))$$

thus, if Y'>Y, the POI does not fall within the target full value area and will not be given credit for falling within this area when scoring. Other embodiments will certainly add a second value responsive to the minor axis thus enabling more variety.

Implementers may choose to use circles, rectangles, ellipses, any number of other applicable shapes to determine if the POI falls within an area close enough to the target coordinates. For the sake of brevity, the circle is used as the example to be explained in depth for most of the discussion herein. However, the fields are provided such that implementers could use one or any combination of the shapes as individual scoring elements each contributing individually to the score if desired.

SpatiallyDeprRespCurve (Integer) This is the optionally formulative score-depreciation response to distance between the target coordinates and the viewer's actual instant POI. Although formulae could be included as a field value here were this a string field, in the preferred embodiment this field is simply an integer representing a formula accessible by the software and identified by this integer.

SpatiallyDeprRespRange (SDRR) (Integer). (SDRR) This is the furthest distance a POI can occur from the circle associated with the target full value radius and still result in any score at all. In other words, the depreciating response curve will not be applied for POI's whose distance from the target coordinates is greater than the sum of the target full value radius and the SDRR.

TimeFactor (Integer). This is an integer identifying the sequence number of a calculation for augmenting scores responsive to the persistence of the fixation. The calculation that the software identifies with his integer includes the minimum and maximum number of contiguous frames in the same vignette having the same meaning attribute and a score magnitude above the same score threshold (described just below) that will be used to raise the magnitude of the score responsive to the persistence of the attribute. The calculation so identified will often be formulaic in order to most realistically value persistence of behavior and to provide variables whose coefficients, particularly when identified through the Monte Carlo process, best reflect the nature of the condition being diagnosed and treated.

ScoreThresholdPositive (Single Precision Decimal, 2). This is the positive score magnitude above which the time factor may be used to further increase the score), ScoreThresholdNegative (Single Precision Decimal, 2). This is the negative score magnitude above which the time factor may be used to further decrease the score), and SkipFrames (Integer). This is an optional integer indicating how many subsequent frames will continue to follow this rule and increment scores with it without having to reread the data file again). This defaults to zero. When the skip frames option is used (when it's value is positive and non-zero), it is not necessary to make or load here subsequent database records for this meaning attribute (up to the number in this field) (making database file sizes smaller and enabling faster processing).

Condition (Integer). This optional value is the condition of the subject upon which this scoring record was based AnchorPower (Integer).

Multiple values for any and all of these corollary data will be normative allowing in any single video frame any number of identified target locations with individualized scores and/or responsive actions. The actual scoring process will be discussed further below.

B Viewer Analysis and Eye-tracking:

There are wide variety of eye-tracking systems. Some, for example, have a single camera or two laterally-separated cameras either located often below the screen (to avoid eyelash interference) as shown in 108 of FIG. 1. Some use facial characteristic algorithms to recognize head positioning, etc. and, in the end, return values that can be read as or calculated to be representative of POI. In the flow chart of FIG. 3 this viewer analysis is re-performed for each frame to most precisely calculate, in addition to other measures, POI. However, for a seated or reclining viewer, this step can, by implementer or user choice, be reduced substantially to once every so many frames to reduce processing overhead.

Figure 3:
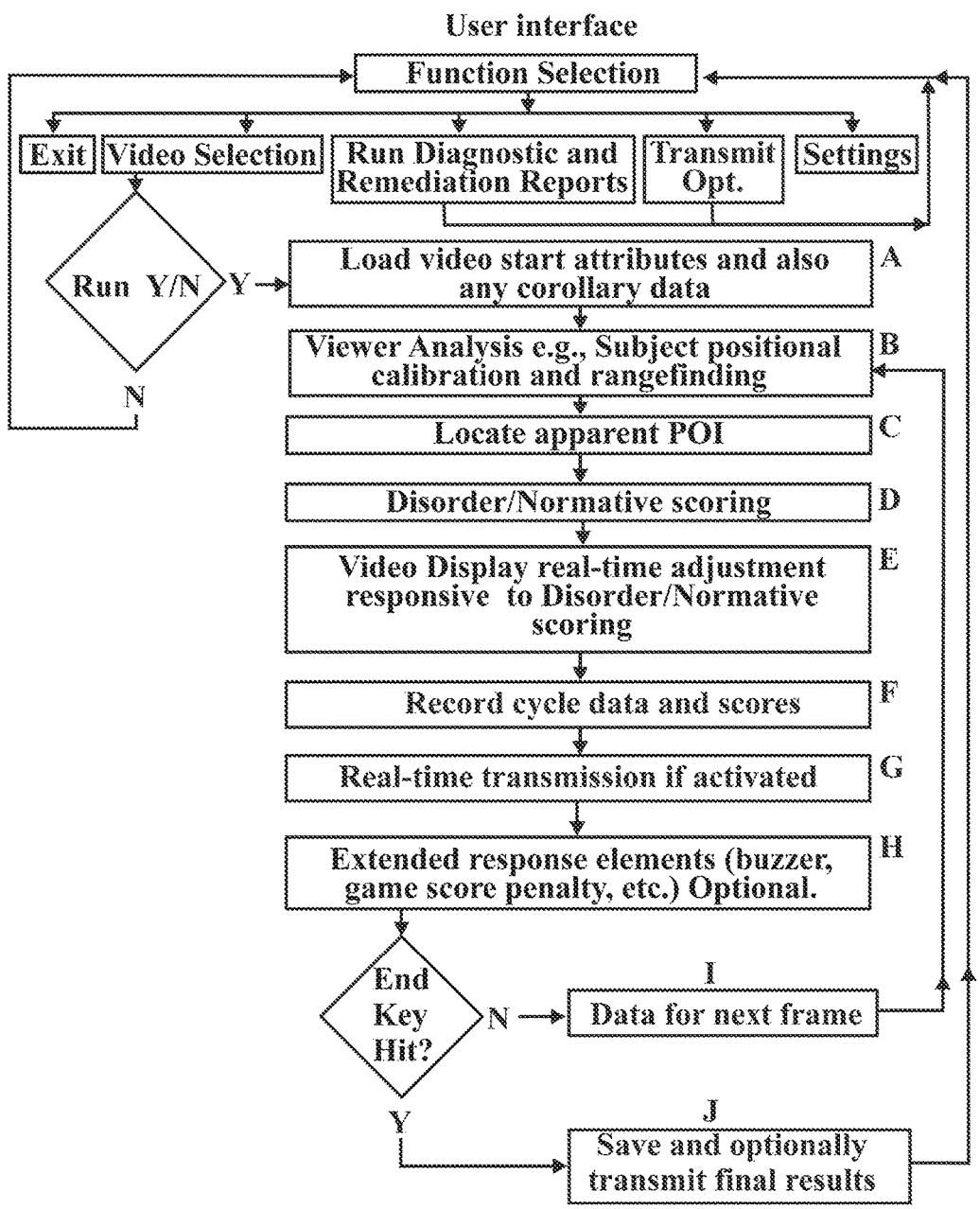
FIG. 3 is a flowchart illustrating exemplary steps in the process of executing the devices and methods of the current invention.

Also, for improved time-efficiency, every execution of this process need not wait to be begun in the series order of FIG. 3 which is simply one example procedure. For example, on the first pass, the initial subject position, orientation, distance to screen and initial POI data may be calculated earlier and in the background (simultaneously with other processes like frame image and corollary data loading or, for example, during any of the scoring steps).

This process, which normally includes reading of viewer position from the camera image(s) of the subject, can actually be an optional feature in some embodiments of the current invention. For example, in lab tests it was adequate for some applications just to have the subject sit reasonably still in a known position (that is, at a known distance from the screen and sitting essentially centered preferably with the cyclopic vision axis, when normal to the coronal plane, approximately intersecting the center of the screen). From this approximate positional data, the angles of the eyes and thus their POI can be approximated in a manner that is adequate for some applications and implementer preferences.

Thus, for such embodiments, the subject may approximately center his or her (the masculine identity will be used herein for brevity) head position in front of the screen at a known distance from his eyes to the center of the screen and either enter, via keyboard or other data entry process, the approximate distance or accept an approximated default value. From the known position of the camera or cameras imaging the eye with respect to the center of the screen, the position of each eye with respect to each camera may be calculated by ordinary triangulation. There are many well-known and applicable methods and devices for calculating the subject's POI from this data and the captured images. Without detailing each here, the location of the subject's fixation is identified.

Additional Calibration:

Often even greater precision and more applicability to broader uses are benefited by this positional data being accurately calibrated. For this further improvement, a calibration session and calculation can be executed ideally prior to watching a video. These eye-tracking and vergence calibrations are known to those skilled in the art and may be as simple as displaying a small circle at a known location (e.g., a corner or at center) on the screen and prompting the viewer to look there. Typically, the software then creates a calibration curve relating any eye-tracked POI to the calibrated value.

There are, of course, alternative or contributing ways to calculate subject position that are applicable to the current invention including but not limited to dual laserbeam convergence, single angled laser beam position, laser Doppler, projected facial grids, sonar, facial feature and feature-placement (eyes, nose, etc.) recognition, etc.

Also, and applicable to both subject positional data capture and location of POI, any alternative means of eye tracking or line of sight indication are applicable to the current invention including but not limited to electro-oculogram signals (particularly for the fast frame rate) and oculo-encephalographic sensing (where the displayed video image itself or components thereof can serve as adequate optical stimulus). All available elements effective for measuring and reporting the positions, or angles, or points of vision-axis intersection (or any combination of these) are understood to be included as applicable alternatives when the term "eye tracking" is used herein for.

In one preferred embodiment, the eye tracking or other line of sight obtaining component chosen by implementers will rapidly and accurately capture the data needed for step B from a plurality of captured camera images often enhanced by additive lighting and powerful software analytics. For example, the Tobii IS-2 Eye Tracker from Tobii Technology AB Karlsrovagen 2D Danderyd Sweden, provides an OEM (original equipment manufacturer) ready module mountable at the bottom of a video display screen and having a published frame rate of 30 Hz with accommodation for substantial subject movement without loss of accuracy.

C. Locate Apparent POI:

Eye tracking equipment, including but not limited to those already discussed, now identifies the POI. In the applications for diagnosis and remediation of autism, this includes the identification of a point or area on the screen.

If the viewer's fixation is not anywhere on the screen, the point of actual eye intersection may be recorded as a virtual position outside of the Cartesian coordinates of the screen but on the same Cartesian plane with respect to the center of the screen as the origin to simplify scoring calculations. While corrections for off-screen discompliance could be effected at this point, in the preferred embodiment, this now-identified POI is captured for action in later steps.

However, in some applications, e.g., strabismus, the viewer's vergence may, in fact, result in a fixation that is significantly more proximal or distal to the viewer than the plane of the screen and this is applied usefully by the current invention as indicated herein.

In the preferred embodiment, this POI location is stored as the value described as the target coordinate in the data structure above. Thus, an X,Y pixel location on the screen itself is thus identified.

D. Disorder/Normative Scoring

There are vast differences in the way different implementers score subjectively interpreted phenomena and, thus, how they will implement the current invention. Thus, providing examples as we do here, while showing a few approaches, probably does a better job of showing how very differently different researchers compile and analyze data. Nonetheless, for one example, let's establish a short vignette for individual scoring made up of a potentially short range of video frames in a longer video. This may be part of a longer continuous presentation but may be scored separately as a vignette. Scoring from multiple vignettes can be used to create a combined score. In the short vignette, we will score based on a simple set of scoring values.

Pre-screened Material:

In one embodiment of the current invention, videos are prescreened by knowledgeable personnel who identify areas in the image and provide for them particular attributes and values responsive to the condition they seek to diagnose and treat.

However, because it is tedious for reviewers to locate and type in long target coordinates, for every frame, implementers will typically include a time-saving user interface for prescreening personnel that allows them to identify an area with a circle or other shape over the area of interest in the image being reviewed with a mouse or other pointing device. Complex shapes may be used in applicable embodiments but this explanation herein uses a circle around the target coordinate location whose radius (the "target full value radius" field described below) defines the area around the target coordinate location at which a POI in that area will be treated as a direct hit (i.e., as if the POI exactly equals the target coordinates).

The software will then identify the central target coordinate location (preferably a weighted "center of gravity" for more complex shapes used in other embodiments but in this example simply the center of the circle drawn over the area of interest on the screen showing the frame by the reviewer) and automatically create a record in this table. That record will have a frame number value driven by the actual frame number being viewed by the reviewer, a target coordinate value driven by the thus-calculated center of the area chosen by the reviewer, and a target full value radius (described in the data structure above) based on the radius of the circle circumscribed by the reviewer.

The reviewer will then be asked to key in or otherwise enter the other data field values below and will simplify the process by making the default value either the same as for the previous record. Where applicable and for faster entry, the default values for the fields listed above, which can be overridden at the keyboard, can be an implementer-chosen value based on the software-recognized nature of the area in the image selected by the reviewer (such as a human eye).

When these are prescreened, the screening personnel assign values for different ocular behaviors for a given frame or frames, based on the displayed actions and elements that occur in those frames, by entering, in the preferred embodiment, data into a database or table for values like or similar to those listed above in the data structure for an example embodiment.

Vignettes:

The beginning and end of a vignette is recognized by a change in the value of the vignette frame-grouping number (a field in the primary database). Thus, (in this particular example of a scoring style) for each frame in each vignette, the software will not only read the databases for the scoring criteria related to the instant record in the primary database (which is responsive to the current frame being scored) but will zero a count variable for each score element at the beginning of execution for each vignette and increment these variables as the vignette proceeds for each credit amount.

A vignette made up of a group of contiguous frames can be a very simple scoring subset of a longer video made up of many sequential vignettes. For example, a series of frames may simply show a scene where a person testing positive for the condition being tested is likely to look during this little theatrical vignette. If the POI occurs in the areas so indicated in the contiguous records having this same vignette number (which defines the length of the vignette), a positive score for the vignette will result.

Multiple simultaneous vignettes can also be used at the same time, even in the same frame to individually score different areas with different scoring attributes.

Scoring Logic:

Since it is difficult and normatively less frequent for those with autism to look at human eyes that appear to be looking at the camera (and thus, perceptively, at them), the area very proximal to the eyes of such a person in the image of a video frame may be coded with an optionally negative value for normalcy. (Obviously, positive values could also be used for normalcy on a similarly applied scale. By choosing to use the negative end of the scale for normalcy, we choose to use positive to indicate a disorder. Thus, a positive result will be understood to indicate the presence, and optionally the approximate magnitude, of the disorder condition recognized.) Thus, if, in this example, the viewer looked directly and precisely in this normalcy area, that viewer would receive a higher magnitude (in this chosen example, a more negative) symptom score.

If the viewer looked in another area substantially away from this anticipated fixation area or in a highly positive area (e.g., far from the normative viewing area and potentially in a highly non-normative viewing area), the implementer could choose to rate that second area with a score more towards the positive. In the preferred software embodiment and reviewer procedure, this second area in the instant frame's image is scored with the use of a second vignette even for this same frame or group of frames.

3 Simultaneous Vignette Example:

Thus, consider an even more complex frame in which the reviewer wants to score the frame using three different areas with their own criteria for scoring. This will be done, in the preferred embodiment, with one primary database record for the frame (and optionally any video syncing information) and three related child records (related by the frame number field that is in both databases) each of the three records having a different vignette number.

For example, the first vignette can be dedicated to an area of the image associated with highly negative scoring such as the screen location of the eyes of an angry person glaring at the viewer. When the viewer looks directly at this area, it is highly non-positive for the dysfunctional condition being tested for and thus has a negative score. Normally, a viewer will not be looking at two disparate areas of the same frame since there are typically 24 to 30+ of them per second, so only one of these three vignettes will receive a score for this frame.

Let's let the second vignette for the same frame regard an alternative area on the same image frame that the reviewer believes should test positive for the condition being tested. Perhaps the scene is set up such that, given the choice of a glaring set of eyes from an authority figure (covered by the first vignette) and the welcoming eyes of a contextually irrelevant dog far from the central areas of action (the subject area of this second vignette), the significantly autistic person will be looking at the dogs eyes. Thus the child database record this frame and with this vignette number will calculate a positive score based on the degree to which the viewer POI fixates upon and persists upon this area.

For the third vignette, representative of the many possible simultaneous vignettes, consider a more neutral area of the image that is nonnormative for healthy viewer fixation. A POI in this area could be reviewer chosen to have a moderately positive scoring value.

Thus vignettes can be used in combination to score individually essentially every area of the screen either positively or negatively.

in this preferred embodiment, if there is, for example, an image area with a negative score in the same group of frames where the reviewer also wants to code another area for relatively positive (indicative of dysfunction) score, Time of Fixation is also a substantial optional criteria applicable to the scoring process. For example, up to an implementer-chosen amount of time, the longer the subject looks at that person's eyes, the higher the resulting normalcy score based on scaling values chosen by the implementer. Just for example, to minimize false negatives, an implementer might choose for the software to return zero or only slightly negative values for healthy fixations of less than 5 frames (or perhaps ⅙ second).

Action and Topical Focus:

For implementers seeking to capitalize on published reports that, in an action frame such as someone pointing frantically in a direction, a person without autism will tend to look at what they're pointing out while a person with autism may instead look somewhere else, those looking at the point of visibly indicated action would receive a higher negative score.

Multiple combinations are obvious as are any number of conditions that an implementer may desire to include in the scoring process. As time goes on, implementer opinions about different stimuli will certainly change and thus the scoring values for areas of a frame will change with them. Thus it is not the place of this discussion to limit the current invention to current numerical values, titles, or criteria for any stimuli or phenomenon but, instead, to provide devices and methods that implementers can use to score responses to stimuli and to use these scores to diagnose conditions and implement remediative actions.

Example Scoring:

An example follows to explain several of the fields in the example database. It is very likely that many if not most reviewers will use only a few of the fields in any given vignette to fit their particular needs for that subset of the video. However, in this example, we will stretch the example a little to allow all of the fields to be used in the corporate scoring of many elements for the same frame. The database fields, format, interface from fields to video (or the absence thereof), and even storage elements may and will be changed by implementers with their own objectives from those discussed here. This is merely an example of how the current invention can be used.

Just to set the stage to help explain this process, we describe a video whose first 20 frames are innocuous enough and have, in the opinion of the pre-screening personnel, no scoring value. Thus no scoring data was stored for the first 20 frames Then finally, in the 21$^{st}$ frame a scoring opportunity was observed and coded. Here is what the 21$^{st}$ frame looks like. The visible background on the screen is devoid of any action elements. At right foreground is an elevated authority figure gazing directly down at the viewer and explaining something intensely. At the opposite and lower corner of the screen is a motionless golden retriever looking approximately in the direction of the viewer. Within the story of the vignette, apprehension of the vivid and communicative expression on the speaker's face is necessary to understand the context of the vignette.

Looking at the database tables (FIG. 7 is one sample embodiment of the database table structure), there are no pre-scored reviewer controls stored for the first 20 frames. In one data strategy there are 20 records in the primary database (associated with the first 20 frames) with no child records because there are no scoring values to be stored in said child database table. (The video reference field may optionally be used to sync with the appropriate video frame, Alternatively, the control software may simply start the first primary record with the 21$^{st}$ frame number. In that somewhat more efficient data framework, the control software reads a primary database record and, if it is for a frame yet in the future, simply waits until the frame whose number is in the frame number field comes up. Still other implementers will implement control software that will not directly command the execution of each frame but will otherwise synchronize eye-tracking, scoring, and video execution. In fact it has even been found practical to simply identify the approximate instant frame number being executed based on the time elapsed since video initiation using the system clock of the high-speed personal computer that runs the control software. However, in the example file structure of FIG. 7, there is one primary database record for each frame and this primary database record is indexed (in a one-to-many data relationship) to point to any number of child records containing scoring information for any number of scoring elements for that same frame. There is also a video reference field in the primary database which may be used for matching video image data and/or providing data supportive of controlling its execution.

Now, as the 21$^{st}$ frame is being displayed, the control software interrogates the 21$^{st}$ record in the primary database and the first matching (related) child database record as illustrated in FIG. 7A. The value of the vignette number field is the integer "1" indicating that this is beginning of the first of vignette's scoring (no previous record had a vignette number). The meaning attribute field has an "11" which arbitrarily, for this example, identifies "interpersonal eye engagement, opposite sex and adult". It is not necessary for the control software to perform any special functions based on this meaning attribute value (there are plenty of control elements in the child database that the control software can use to grade the viewer). However, implementers will inevitably add special grading elements for certain meaning attributes and this also provides a handle to facilitate that.

Figure 8:
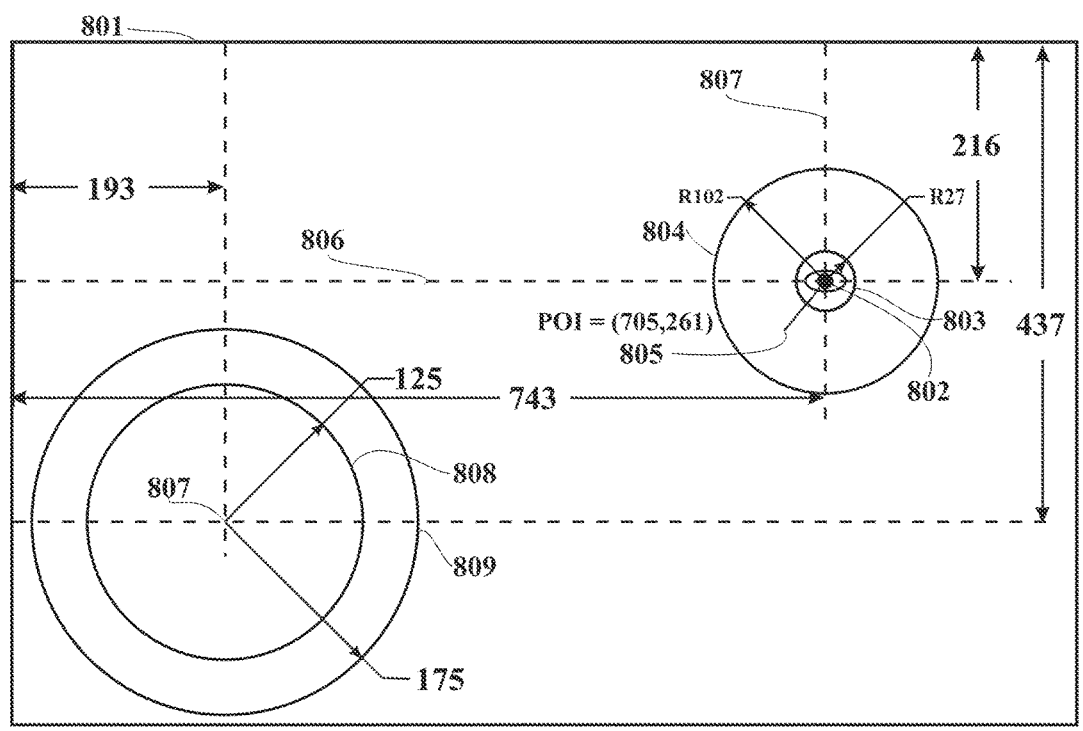
FIG. 8, FIG. 9A and FIG. 9B support the discussion in the specification of an exemplary process for scoring the values responsive to the importance of the observer looking at different points on the screen. The center points of the two exemplary sets of concentric circles shown illustrate two exemplary points on the display associated with a given tendency. The distances between each such point and a point representative of the observer's instant point of focus are related to the score.

The target coordinates in this example (00743,00216) are the location of the left eye 802 of a right-facing adult near the top right hand corner of the screen 801 as schematically illustrated in FIG. 8. (For the sake of space in FIG. 8, the number of pixels on the screen schematically illustrated does not necessarily match the pixel density or aspect ratio of many screens.) Using location attributes beginning from the top left hand corner of the screen, the target coordinates are 743 pixels to the right and 216 down. In FIG. 8 this can be seen as the intersection of the two dotted lines 806 and 807 which are illustrated to cross those coordinates.

The target strike value is identified as −41. Here, in this example, the pre-screening personnel appear to have assigned a negative value for the condition when the viewer precisely engages the eyes of an elevated adult member of the opposite sex ostensibly presuming that it is not indicative of a positive diagnosis for autism in the scene of the instant frame. Screening personnel will, of course, establish their own scales based on experience, changing understandings, and computer analysis-generated values that will be discussed later.

The target full-value radius field has a value of 27 pixels in the data field shown in FIG. 7A. It can be seen as a circle 803 of radius 27 surrounding the target coordinates. Let's presume that the viewer's POI, 805 in FIG. 8, was at (705, 261) as drawn (805) and thus fell outside that target full value radius 803. Thus, since the POI missed the circle 803, the score is not affected by the −41 target strike value—yet.

However, prescreeners may assign a lesser value (a Depreciating Range Score) for nearby areas. Only one example of the many applicable approaches for this is illustrated based on the spatially depreciating response curve field in the child database whose value is "3" in the example shown in FIG. 7A. That number simply identifies an algorithm chosen by implementers and known to (i.e., operable by) the control software. The control software uses a logarithm-based algorithm, identified as 3 in this simple example, to depreciate the score over range of about 75 more pixels based on the purely exemplary equations:

$$N = ((ABS(X_{POI}) - ABS(X_{TARGET}))^2 + (ABS(Y_{POI}) - ABS(Y_{TARGET}))^2)^{0.5} - TFVR$$

$$DepreciatingRangeScore = target\ strike\ value * Ln(2*(SDRR-N))/5$$

where Ln is the natural logarithm, $X_{POI}$ and $Y_{POI}$ are the coordinates of the instant POT, $X_{TARGET}$ and $Y_{TARGET}$ are the target coordinates, TFVR is the target full value radius, and SDRR is the Spatially Depreciating Response Range. Typically, this will only be executed when the instant POI falls outside the range of the target full value radius during the display of this example frame (since a hit within the target full value radius gets full value). The value N is the distance in pixels between the circle for target full value radius, 803, at the POI.

Thus, in this example, full credit is given within the target full value radius and immediately beyond that radius begins to drop off with an exemplary function here which ceases to give any credit at all after about 75 pixels (the SDRR in this example) from the full value radius circle (the outer periphery of the scaled credit is illustrated by the Circle 804 whose radius is 102 since the target full value radius of 27 plus the 75 pixel range of the spatially depreciating response curve equals 102 as the radius of 804 is so indicated). In this particular POI example, N=32 (pixels are rounded) and the target strike value is thus multiplied by about 89% thus the score is about 89% of −41 or −36.5 (which, if by itself, would be contraindicative of the condition). Numerous other scoring elements and values will be used, these are simple, examples of approach only. Other algorithms will, of course, use rectangles and other area parameters.

The target time factor will be a factor in subsequent frames.

The score thresholds were set to 2 indicating that time-based scoring will only occur when the other score for the instant meaning attribute already exceeds 2. This will be used in the next frame.

Had Skip frames been a positive integer, these factors would also be applied in that many subsequent frames. Since Skip frames is entered as zero in this example, these exact criteria will not be applied to the next frame but will require an additional database record (or many of them) if the implementer wants to continue this meaning attribute in this vignette to (or beyond) the next frame.

For the $22^{nd}$ frame, there are two child database records indicated in FIGS. 7B and 7C. The first new child record finishes the vignette #1 that we just began scoring in the $21^{st}$ frame (extremely short vignettes are considered here for the sake of brevity) and the second additional child record begins a second vignette. Both vignettes are actively scored for this second frame. Of course at the implementer's option, the second of these child records, FIG. 7C, for Frame 22, could also have been scored in the same (first) vignette. Even in this abbreviated example, there are two meaning attributes being simultaneously scored in the $22^{nd}$ frame and there can also be many. Thus, any number of meaning attributes can be scored simultaneously in any frame, over any number of frames, and as part of mixed vignettes. The impacts of this multi-dimensional scoring approach will be seen to be especially useful when using the Monte Carlo optimization.

Thus, in 7B, the only field that has changed is the frame number and a slight change in the target coordinates because of slight movement of the target, here the left eye of a right facing person (right eye hidden), between frames. The time factor is 5 which, in this example, is simply the number of an implementer-chosen formula for valuing the length of the period of fixation. Thus, if the score for this meaning attribute has been above the magnitude of the score thresholds (shown as 2 in this example) in a plurality of contiguous frames, a bonus to the score based on the implementer-chosen time factor formula is added to the score for this meaning attribute. Thus, this is one means of valuing longer fixations during periods where that persistence of fixation is indicative of a tendency towards the meaning attribute.

The score for vignette 1 will be totaled when the control software recognizes the absence of meaning attribute 11 in the child table for a subsequent frame. In this short example, we will let the Primary Database Table for the $23^{rd}$ frame have no related child database records for meaning attribute 11 and thus the scoring for meaning attribute 11 will be closed with whatever score had accumulated up to and including the previous (here the $22^{nd}$) frame. In the scoring for the $22^{nd}$ frame, because the score exceeded the score threshold magnitude (here a negative one, −2), any implementer-chosen credit algorithm for time factor 5 will be applied.

In FIG. 7C we see the second child record related to the Primary Database Table having FrameNumber=22. Thus, a second vignette, #2, will also be scored for this frame. Briefly, the target coordinates indicate for vignette number 2 in this frame a full credit for when the POI occurs at 807 in FIG. 8 or at least within the target full value radius of 125 shown by circle 808. If the POI misses this but falls within the SDDR circle, 809, a partial credit will occur. These credits will be positive based on the target strike value of +38 since the implementer in this example assessed this area to be indicative of where a person with the condition being tested might look.

Again, any number of areas may be scored for each frame. In fact, every pixel on the careen may have a positive or negative value associated with the POI occurring there. These scores can be summed by meaning attribute, vignette, and full session. Each time the control software scores a frame and finds that a previously executing vignette has ended (since it is not represented in this frame), the scoring for the vignette may be totaled and cross tabulated in any number of combinations with other values per implementer preference.

It would appear that this explanation of only one of many data structures and control program operations applicable to the current invention is excessively extensive. Indeed, many will use, alternatively or additively, rectangles or other complex shapes to identify areas and range values from a point or points within them, often causing the target coordinate to be the "center of gravity" of even very irregular such shapes on the screen. However, this excessively extensive description of example fields and their uses will be further usefully applied to explaining both the optimization process and non-pre-screened embodiments further below.

E. Video Display Real-time Adjustment

In the simplest and preferred embodiment, the video display is now adjusted, unless implementers prefer to use the extended response elements in step H of FIG. 3 instead, responsive to the score for the current frame. There are a number of practical and effective responses known to be effective for the remediation of certain conditions and other applicable ones will arise.

The mechanics, applicable to the current invention, of degrading the video image to motivate the viewer are too numerous to list. Any equipment or process that can be directed to modify an image is applicable. For example, in the simplest embodiment, an ordinary desktop computer with a hard drive, video card, screen, and software to degrade the image before it's displayed can fill the equipment-based roles of processor, data source, video controller, display device, and image degrading element (listed respectively). The image degrading element can also be a hardware device placed between the video controller and the display where the processor is operatively connected to that hardware device in order to adjust the amount of image degradation.

Defocus

Defocus has been shown to be a powerful stimulus for corrective eye fixation. Much of the brain's processing capacity is dedicated to the full apprehension of captured visual images and brain plasticity has been observed aiding in the improvement of dysfunctional eye-fixation conditions. Responsive to an adequately positive score, the image is blurred. In embodiments similar to the one shown in FIG. 1, there are a number of ways known to those skilled in the art to do this. Perhaps the simplest is to use software utilities (e.g., the Intel toolbox for video processing) called by the running control software for a degree of defocus relative to the score. In worn embodiments similar to FIG. 5 and having electronic focus control, e.g., electro-optic lenses and spatial light modulators (SLM), defocus can be applied to even very portable embodiments and optionally to embodiments requiring no pre-screening.

Color Deprivation independently or in coordination with other image degrading

Localized Defocus

The area of defocus can also be confined to an image area implementers desire to highlight or direct the viewer's attention away from. For example, the responsive real-time adjustment of step E in FIG. 3 for a an autistic viewer watching an area indicative of a positive score (meaning the presence of the malady), that area may be defocused. In programming terms, using the program code snippets of FIGS. 11-13 and the much discussion regarding them, this area to be avoided (and thus locally defocused) may be described as the area "covered" by scoring anchors (e.g., from the file ScoringChild) having highly positive Target-Strike field values). These anchors are also referred to herein as target locations. The actual areas thus defocused are the areas centered around the TargetCoordinates location and surrounding area within a radius of the sum of the values for TargetFullValueRadius and SpatiallyDeprRespRange. The degree of defocus within the TargetFullValueRadius may optionally be higher (optionally based on the value of the TargetStrikeValue) than just beyond the circle with that radius but still within the radius that includes the SpatiallyDeprRespRange (optionally based on the values from calculation of the SpatiallyDeprRespCurve).

Localized Focus

For example one desired remediation cue for autism benefits from an ability to both limit vision to stimulate a change in POI and to indicate where the subject should be looking by the location. Thus, a stimulation cue for strabismus to direct a viewer to look at a certain area may be a general defocus of the image except for a localized area where implementers want the viewer to watch. Programmatically, this sharp focus in the preferred area of POI location can be effected similarly to the Localized defocus discussed just above here except, of course, that the area selected using TargetCoordinates fields, etc., would be based on areas defined by scoring anchors having very negative (i.e. desirable) values for TargetStrikeValue (as opposed to the positive values preferred in the previously explained defocus example).

Diplopia

Similarly, software-directed diplopia is a powerful incentive for correcting fixation and, for that matter, stopping whatever else it is you are doing appears to be causing it.

Vignetting

Vignetting is a powerful option that not only spatially indicates (at the center of the vignette area) either the current point of fixation or the implementer suggested point of corrected fixation (depending on implementer preference). Applicable to being used at a gradient, the degree of correction required can be thus be proportional to the peripheral visual obstruction driven by the magnitude of the vignetting. As is discussed elsewhere herein, this can be especially useful in embodiments where the viewer's forward view is important for perspective, navigation, or spatial perception. The narrowed field of view through the peripherally shaded view, whose effect to "aperture" and the darkness of the peripheral shading are responsive to the degree of the condition to be treated. For a person with autism, for example, the center of the vignette can be over the suggested viewing area forcing the viewer to look where he should in order to have good vision. In another example for a person with strabismus, the location of the suddenly-appearing vignette's center tracks the position of the weak eye rather than the strong eye forcing the user to direct his strong eye in order to have good vision.

Dimming or Blanking

Dimming or, perhaps for extremely highly positive scores, blanking the image altogether also forces the viewer to correct undesirable visual fixation. In embodiments applied to strabismus, this dimming can be directed to occur selectively in only the strong eye analogous to conventional treatments. In portable embodiments, this can be accomplished with shelter glasses and for HUD's and interference projected image has a similar effect as discussed elsewhere herein.

Targeted Direction

When a POI occurs in a highly positive scored area of the image, the image display (whether it is a monitor, heads-up display or other display) simply displays an overlaid image over the normal image at a location in the image that the implementer selected to be behaviorally didactic. To use an earlier example, when the POI falls upon and area of the image normative to the condition being treated, a crosshair, circle or other indication over or around the preferred (negative) area leads the viewer to a behaviorally improved POI. In the preferred embodiment using targeted direction, highly interruptive, blinking, spinning and otherwise attention drawing targets are used.

F. Record Cycle Data and Scores

The score is recorded enabling later cross tabulation of data over multiple vignettes and combined meaning attributes.

G. Real-time Transmission

Optionally, the data can now be transmitted wired or wirelessly either in real time or in batch mode to caregivers for analysis.

H. Extended Response Elements

As optional replacements for or augments to the above video display stimuli, extended response elements are effective means for communicating both function specifics and magnitude of importance. For example, a given sound or even verbal audio message, produced by a common voice simulation circuit and a small speaker in any of the embodiments considered herein, can indicate a specific recommended response to underscore or explain a visible corrective stimulus. They can also be used to underscore the importance of the stimulus; particularly when the viewer has been inadequately responsive.

I. Next Frame

The keyboard or any other user interface element is then interrogated to see if the viewer has indicated a desire to stop the video. If not, the next frame is begun and the cycle repeats typically with step B in FIG. 3.

J. Save and Optionally Transmit Final Results

If the viewer has indicated a desire to stop viewing, the user interface returns to the main menu.

Non-pre-screened Scoring:

Software for locating faces in an image and identifying the location of eyes, noses, facial orientation, other body features, and even building and landscape features is well understood. It is also possible to estimate the distance to the person being viewed based on the distance between their eyes being recognized. This software is often a modular feature for camera image acquisition software. For example, this image element recognition software module (IERS) is commonly used with camera ranging and focusing software modules. It identifies an area in the viewing field of view (FOV) where, for example, it recognizes and locates the eyes of one or more people. The focusing portion of the camera software, responsive to this data for such location(s), can set the camera focus to the distance sensed for that location by the range sensor. Adding an IERS module to the control software of the current invention is straightforward and understood by those skilled in the art and thus will not be extensively explained here. In embodiments of the current invention including this optional element, the software can interrogate and score, not unlike the scoring above, any video image and, where desirable, do so in real time.

Positive Reinforcement

It would be unfortunate if the current invention only provided negative reinforcement. Of course, the sudden absence of any of the negative reinforcements listed above responsive to a subsiding of an adverse behavior is in itself an instant positive reinforcement. In the preferred embodiment, all stimuli are responsive on a gradient. That is, the more adverse the behavior, the greater the magnitude of the corrective stimuli. Similarly, the more healthy the behavior the more positive it should be. In fact the breadth of that gradient in negative stimuli can be expanded with the addition of additional positive stimuli.

Many of the same attributes perceived as negative stimuli may be chosen to be especially enhanced when the calculated scores are not only not adverse but are very healthy. For example, in the presence of very healthy behavior, image color may be especially enhanced beyond a slightly dull default value, surround sound can replace a single speaker, music can accompany an otherwise quiet video, and the size of the image on the screen can be increased from the smaller default value to full screen.

Seated Real-time Applications not Requiring Pre-scoring

In an embodiment like FIG. 1, the scoring software hosted by the computer 109 performs the IERS modular function on each frame of video being displayed on the screen 102 and reports recognition locations and identifications to the scoring module) while recognizing the POI through the eye-tracking module 108.

The scoring software, thus advised of a recognized pattern's location and identification, scores based upon implementer-provided criteria as is detailed herein.

For example, consider a single table (similar to or identical to the child database discussed above except without frame number, vignette number, and skip frames and indexed by meaning attribute. Here, for example, we consider a meaning attribute number 107 arbitrarily chosen here to score, where applicable, a POI at or near a recognized pair of eyes. Then, in real time, the IERS locates a set of eyes in the camera image being viewed and passes the displayed image coordinates of a central location representative of that location to the control software at the same time that the eye-tracking module provides the coordinates of the location of the POI. The scoring module of the control software then looks for a record with a meaning attribute field value equaling 107. In one example embodiment, the implementer has chosen to provide a higher target strike value for eyes recognized and located above the center of the screen analogous to looking up at someone. Thus, if one of the records with a 107 in the meaning attribute field has a target coordinate TargetFullValueRadius (or width and height for embodiments including the rectangular area identification) inclusive of the instant POI the scoring feels that record can be used to score the instance as described herein. Responsive corrective stimulation can, then, be effected in real time.

It should be noted that scoring does not need to use a database approach but, as is obvious to those who write software, can be hardcoded to recognize and score a POI in any area of interest with a software-designated value. Also, distance to subject may also be a factor considered for scoring. For example, a person fearful of or reticent at eye engagement may find it even more difficult to achieve that engagement close-up. Thus, where either rangefinding sensors are provided and operatively connected to the control software or where ranges are estimated based on inner-papillary distance (or inter-eye-socket-center distance or other means) scoring criteria will be amplified (normally multiplied by a conversion factor greater than one) to be higher for nearer distances than for far distances and that, in the preferred embodiment, along a gradient responsive to the distance. Also, where attention is part of the score basis, when a POI occurs far beyond the location of the image, that may also be included (scored) towards a more positive score.

Even in this non-pre-screened application of the current invention, remediative action may be accomplished in real-time responsive to the viewer's POI. Thus, in response to a highly positive score (magnitudes chosen by implementer), any of the remediative responses described herein for step E of FIG. 3 can be applied.

Worn Real-time Applications not Requiring Pre-screening

Figure 5:
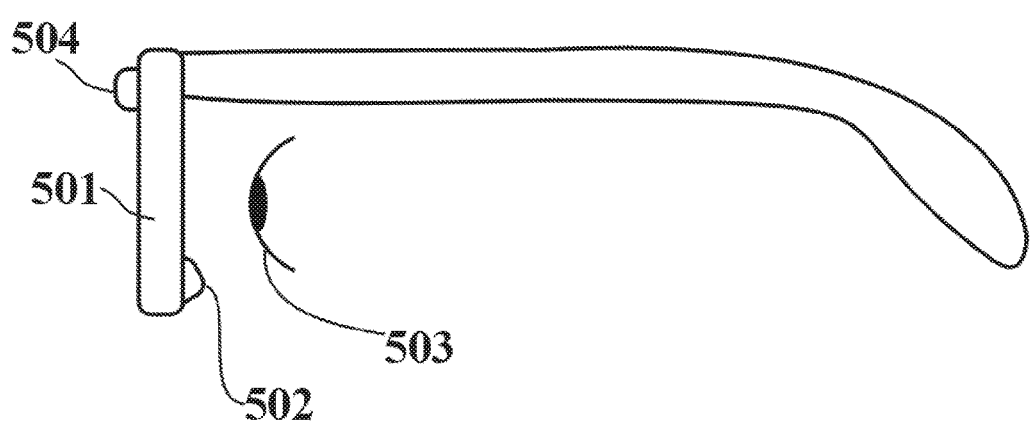
FIG. 5 illustrates a worn embodiment wherein the eye is tracked by camera, 502. The worn assembly may include a forward view camera 504.

In one embodiment a viewer-worn camera (e.g., a worn hardware assembly including a forward camera like 504 in FIG. 5 and an eye tracking camera 502 or alternative embodiments not unlike the Google glass forward view cameras worn like or mounted to glasses) is operatively connected (by wire or wireless communication) to a scoring computer hosting the scoring software. In the preferred embodiment, all of the components are miniaturized and as is broadly available.

Applicable to both autism and strabismus, the playing video in a worn, real-time embodiment, is simply replaced by the live image feed of the forward camera. However, these live cameras also have frame rates and these, or any other time-based delimiters, serve the same function as the frames in the other examples. In the preferred embodiment, the forward view camera image comes from a worn camera like FIG. 5 and, along with the eye tracking camera data from 502, is connected wirelessly or wired to a worn processor (not shown). The software running on the processor recognizes patterns (e.g., eyes with noses and hands using IERS) and, based on the POI's proximity to a central point in that recognized pattern, scores a positive or negative result as discussed herein based on an implementer choices and the condition being diagnosed and/or treated.

Whether the application is for strabismus, autism, both, or for other applications, all such embodiments will provide, responsive to a positive score, (even though that positive score is calculated differently for different applications as discussed herein) a corrective stimulus. The magnitude of that stimulus is responsive to the magnitude of the positive score, normatively affecting the ability to see the forward view but sometimes additively or alternatively including other stimuli like sounds.

For example, when the application is for strabismus there are a number of real time obtainable indicators for both the presence of binocular infidelity and its magnitude. For example, when one eye moves and the other eye does not, when there are differences in eye elevation as opposed to the two vision axes at least essentially sharing a transverse plane, all of which are easily obtained from eye tracking software in some of which are already provided in that form by the eye-tracking software.

When the eyes move in different directions e.g., one to the left and the other to the right Eye elevation, as discussed above, is an indication of binocular infidelity.

Also, esotropic strabismus is easily recognized by the exceptionally close intersection of the vision axes as reported to the control software by typical eye-tracking software (alternatively reported as distance to vergence).

Exotropic strabismus is similarly recognizable when excessive distance to target calculations occur are received from the eye-tracking assembly.

Inactive/active partners: When one eye moves and the other does not, this is an indication of dysfunction.

Responsive to a positive instant score (indicating the presence of the condition to be treated), the wearer is equipment-stimulated to adapt the behavior. If the worn assembly includes electronically focused and/or image-shifting lenses (e.g. electro-optic), defocus or diplopia as described elsewhere herein can be used. In this case, the control software, operatively connected to the electro-optic controls for the electro-optic lenses, instructs the electro-optic controls to shift the focus along a gradient responsive to the magnitude of the positive score.

Where the worn assembly includes shutter glasses, the image may be dimmed or blanked responsive to the magnitude of the positive score as is commonly understood and practiced by devices implementers whose devices communicate with shutter glasses to determine their periods of transmission and periods of closure. However, in any embodiment where the user needs to navigate (particularly with such a potentially portable embodiment where the viewer walks around unrestricted), vignetting or targeted direction are preferred corrective stimuli.

A related embodiment involves any form of heads-up display (HUD). In the preferred embodiment, the HUD places the displayed image over a forward view. One example of this is reverse projection allowing a projected image to be seen "over" the view through the glass. As above, the forward camera captures the forward view and the eye-tracking camera, similar to 502 in FIG. 5, and software locate the POI. The portable processor hosting the scoring software and connected by wire or wirelessly to both cameras and to the worn imaging display places a targeted direction symbol/icon or location-indicating vignetting over either the instant POI (which best allows the wearer to see the forward view) or over the suggested point of fixation (determined by implementer preference and application).

However, in the preferred embodiment of a worn assembly intended for portability (where the processing computer is also miniaturized and worn) remediation responses that favor continued and safe navigation are used. For example, one response is a blurring (defocus) of the image responsive to the magnitude of a positive score. But when the viewer is, for example, walking, central vignetting (permitting a gradiently applied and slightly narrowed FOV around the instant POI) or targeted direction overlays allow the viewer to see where he is going while still recognizing a compellingly visible negative response. Other alternatives include sounds and other stimuli.

Non-Subjective Multi-Factorial Optimization: Applicable to any Disease w/ Significant Effects on Eye Vergence, POI Selection, or Persistence of Fixation The ostensibly excessive description of data fields and scoring details above was thus detailed to also provide breadth in the reduction to practice of target capture in an image, the process of valuing it, and scoring the effects of a plurality of simultaneous points of interest as well as to facilitate the explanation of both optimization procedures and scoring for alternative embodiments.

With that data structure in mind and an understanding thus accomplished of the effect of field values, we now consider another layer of function and process associated with both recognition of new and unknown (typically less obvious) condition signatures and the optimization of a system for applying them to more reliable diagnoses and more effective remediation.

The current process for identifying dysfunction signatures in the massive amounts of data from clinical tests tends to be both random and empirical. The conventional process for quantifying the importance and value of dysfunction signatures as well as their multivariate impact on other related signatures is even less scientific and even more subjective. Eventually, with much experience, clinical researchers will observe what is essentially only the tip of a much larger iceberg in only the most obvious of signatures. The relative and comparable weight to be appropriated for each of the potential legion of such signatures (many of which are still beneath the scientific radar) is extremely difficult if not impossible to apprehend. Grasping, much less applying, the interrelation of these many signatures, including their constructive and destructive interference in augmenting or attenuating each other's observational significance is beyond the pale of even the most diligent of researchers.

However, the data capture assemblies, predictive stimulus, complexity-independent data structure (able to deal with any number of physiologically revealing attributes and their signatures simultaneously in a single frame or other increment of time), and the plurality of simultaneous scoring methodologies of the current invention together provide the foundation for a second layer device and process for automatically converting clinically captured data into statistically verifiable, unbiased, and non-subjective scoring tables. These new, novel, and clinically-derived scoring parameter tables (SPT's) of the current invention in coordination with the scoring methodologies of the current invention thus enable a process for developing the first scientific device and process for statistically verifiable and unbiased identification of even a large number of interacting and potentially mutually interfering physiological signatures. These can be applicable to any malady significantly affecting orthophoria, normative vergence position acquisition, and/or qualitative target selection (selection of a POI based on a conscious or subconscious preference for the identity, nature, or location of the target).

Clinical-Capture for SPT Development; an Example:

Consider first a video that has not been pre-screened (and will not need to be prescreened by a human). However, using processes and procedures well known to those skilled in the art, the video is displayed on any of the display mechanisms discussed while the viewer watches and the POI locations are captured on a frame by frame basis. In the embodiment that is simplest to explain, the assembly of FIG. 1 is used. From well-established and long-term clinical evaluation, a research population is selected, including known healthy and known condition positive subjects, and each clinical research subject is hierarchically rated relative to the magnitude of their condition. For simplicity in this explanation, however, we will simply break the research population into four groups based on subject condition (here in increasingly positive order): 1) healthy, 2) high-functioning positive, 3) positive, and 4) severe. However, more levels will often be used. (These overly general terms are used because there are a number of different conditions applicable to this use of the current invention.)

Step One: Subject Data Capture:

While each subject watches a series of preferably contiguous video vignettes, their POI's on the screen are captured and associated with the instant frame. In an exemplary database for storing this captured data, the field structure can be as lean as illustrated in FIG. 7D.

Many implementers will prefer and use arrays over the database structures used herein but the database structures are an easier way to explain the process.

I. Step one Parent table: (indexed by subject condition)
II. subject number (Integer)
III. subject condition (Integer) (e.g., 1 for healthy)
IV. Child table: (indexed by subject number+frame number)
V. subject number (Integer)
VI. frame number (Integer) and
VII. target coordinates (String, 10)

The addition of vignette number may be desirable for some implementer's to aid in the later process identifying the meaning attributes associated with points in each vignette but this is not a necessity. For each testing subject a parent table record is created and for each video frame watched by the subject a child record is created. These tables with the indexes shown are especially useful for managing step one data particularly during the early data capture process which can require and extended period of time. It can optionally also be used to support additional display software that allows clinicians during step one to view the video and see the subject's POI's indicated over the video image with crosshairs, etc. in real time. However, a separate set of database relations or structured query language (SQL) calls or equivalent methods may be preferred for step two.

Step Two: Pattern Convergence Recognition (PCR)

There are a number of optional and applicable methods for accomplishing PCR and at least two of them will be described as examples herein. The first approach (Approach A) is extremely didactic for an understanding of the logic and principles behind the second approach (Approach B). Similarly, the programmatic elements later described for Approach B are didactic in understanding the practical programming for software automation of Approach A. The automated results of both Approach A and B can be used for later scoring of new subjects or may be optionally optimized, as will be described below, for improved results.

Approach A for PCR:

In the second step for SPT development, which typically occurs after all of the step one capture is complete, the subjects have gone home, and we now prefer the above data in different relationships supportive of PCR. This can be accomplished through additional indexing relations, conversion to a different database structure, an SQL selection or other equivalent step(s), as will be understood by those familiar database programming, accomplishing the same goal of the following data structure preferred for this first example of the PCR process:

SubjectCondition
FrameNumber
POICoordinates
sorted, selected, or indexed in order of SubjectCondition+FrameNumber.

A less lean database structure may also be used to provide better backtracking ability and is described in this example.

Then, step two PCR software interrogates each record having subject condition equal one (since these are in order of FrameNumber+SubjectCondition and we start at the top of the file) starting with frame number one and SubjectCondition=1 to start considering some POI's from healthy viewers. Recall that for each singular frame number there will be as many records with POI (target coordinates) data as there are subjects with subject condition=1 (and the same for the other condition levels). Thus, for each of the potentially numerous records with subject condition=1 and frame number=1 there is a POICoordinates field value indicative of one subject's POI on that singular frame.

In an optional researcher-directed next step, a density map, understood by statisticians, may be created. This may be thought of as a dot plotted at the target coordinate location for each such record having SubjectCondition=1 and FrameNumber=1 on a Cartesian map like 903 in FIG. 9A conveniently having X and Y coordinates equivalent to the number of lateral and vertical pixels respectively on the screen and beginning at the top left corner for 1,1. Thus, a record having target coordinates 0074300216 would be plotted as a dot at the location indicated by 901 (leading to the center of the concentric circles) in FIG. 9a. The above referenced records, all for POI's for healthy people in frame one, can be seen as plotted in the dots like 901 (located at 743, 216) and 904 in FIG. 9A.

Figure 9A:
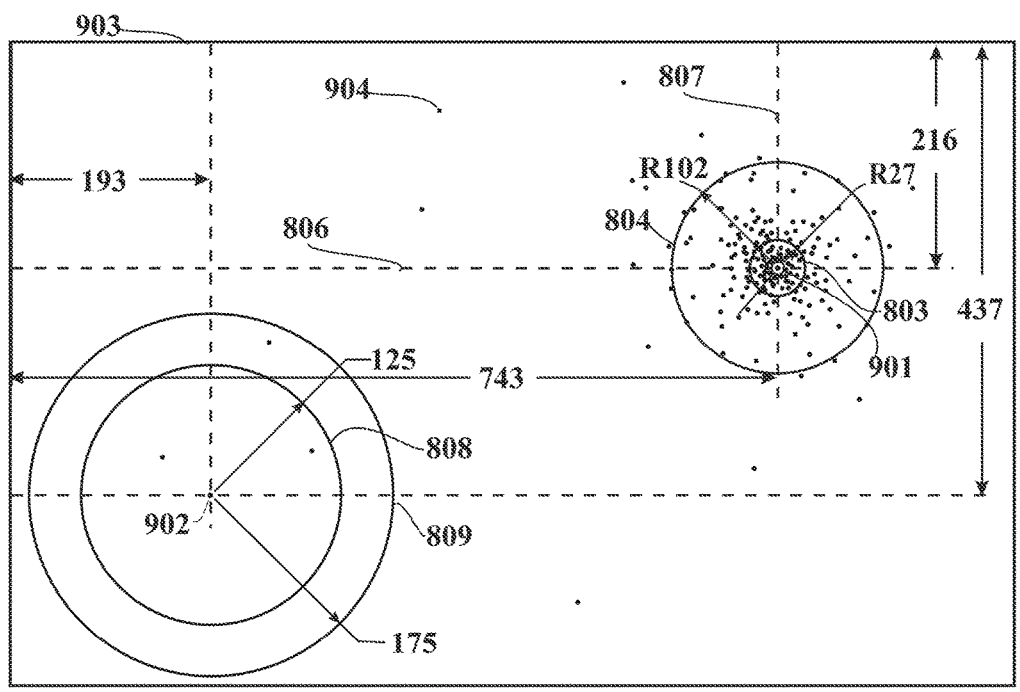

The concentric circles like 804 and 803 in FIG. 9A together serve as a scoring factor or "anchor" (because they define a fixed and visible container securing/containing the POI dots). Thus references to anchors herein point to scoring elements in a scoring template like 803 and 804 in FIG. 9A and to their representation in scoring databases (e.g., ScoringChild in FIG. 11).

Because eye-tracking equipment and displays vary by resolution and in different dimensions, implementers will, where any differences in x and y pixel density is sufficient to create any significant accuracy issues, need to adjust the values so that those values are equivalent as is understood by imaging personnel, Location and Calculation of Target Full Value Radii and Spatially Depreciating Response Curves (Also Referred to as a Declining Power Function which is a Nomenclature that is Inclusive of Both Curved Depreciating Responses and those that are Linear):

The target full value radius for healthy people for this frame (which may later be used with or without further optimization in scoring recognition of negative traits for the condition) may now be identified using statistical methods for density pattern grouping influenced by individual implementer preferences. For example, areas of density in the most concentrated of areas can be identified as illustrated by the circle 803 in FIG. 9A (or the rectangular, elliptical, and otherwise shaped equivalents thereof). The radius of this circle will vary by implementer preferences and, for example, can be based on the radius required for the circle 803 to encompass one standard deviation (of the number of POI's for the condition level) divided by the number of identified target areas. For example, in FIG. 9A, the clustering of the dots indicates that there is only one target area almost completely encompassed by the small circle 803 in the larger circle 804. Thus, for N qualifying records (indicating, in this example, that they were N healthy subjects), the radius of the circle 803 may be chosen such that the circle 803 encompasses Q dots where:

$$Q = \sigma/T$$

where $\sigma$ is the standard deviation presuming a Gaussian distribution and T is the number of targeted areas like 803 (of which we have only one in this illustration). Thus, if N=100, 803 has been thus selected by the containment of 69 dots (FIG. 9A is for general use and does not have 69 dots in 803.) This usable, yet pre-optimization, radius value may now be used as the target full value radius for the first meaning attribute of frame one.

Similarly, and again as only an exemplary calculation, the radius of the larger circle 804 associated with the spatially depreciating response curve, may be driven by the FWHM of the distribution divided by T or, in this example of N=100 and T=1, i.e. barely big enough to contain about 76 of the dots.

Whatever values are chosen by implementers for defining these areas of containment, they may also be further adjusted an improved in the substantial optimization process that optionally follows.

Calculation of Target Strike Value:

All of this process is repeated for each of the groups (in this example: 1) healthy, 2) high-functioning positive, 3) positive, and 4) severe) to obtain different results with different scoring values based on the known groups. Although the target strike values for the healthy group will typically be negative, the values for the other groups will typically be positive for the meaning attributes associated with the containment areas thus defined. Further, the numerical magnitude of the target strike value assigned is responsive to the level of the group. This is one reason why more than these four sample areas will often be used. For example, 10 levels of stratification from negative to highly positive will logically be associated with 10 magnitudes of target strike value thus first defining the target strike values by the level of the group. Within the level of each group, implementers may also adjust the target strike value by the density towards the centers of confinement areas. In the example above where the target full value radius was driven by the standard deviation, the larger the circle 803 has to be to confine those first approximately 69 dots, and similarly the larger the circle 804 has to be to contain the FWHM, the less tightly clustered the results are. Thus, for the healthy group (#1) and where those circles center around a set of eyes looking at the viewer and where the condition being analyzed regards autism, a less tightly clustered result may result in a lower magnitude negative score. While there is still some subjectivity on the front end, albeit by those skilled in the field, the optimization process that optionally follows is designed to remove subjectivity.

Recognizing and Responding to Many and/or Large Confinement Areas:

Scenes will typically be selected by implementers to encourage a singular area of fixation in a relatively small area like 804 determined by negative (healthy) subjects and a singular area of fixation determined by positive subjects both being responsive to action or evocative key scene elements. Nonetheless, some groups of frames will unavoidably allow idle time resulting in more than one area of primary focus for known healthy subjects and one area of primary focus for subjects known to have the condition. When that is the case, the dot patterns will not be tight but, instead, spread out resulting in spatially large confinement areas. This is numerically and visibly observable as a large target full value radius, here driven by standard deviation, illustrated spatially here as 803 and/or a larger 804 driven by the particular spatially depreciating response curve algorithm used, which in this example based 804's size on FWHM. Where these spatially driven numerical values are very large, there may be much less meaning or data reliability associated with them so implementers can simply respond by providing no scoring records for those frames thus making those frames irrelevant to the score.

Also, and separately, there will, of course, also be many scene conditions where it is simply normative for any given subject to look at more than one confinement area and yet there is significance to each of that plurality of confinement areas. When that is the case, those confinement areas will be more reasonable in spatial size (smaller than the meaninglessly large ones just discussed and dismissed) and there will be a plurality of them. For example, there may be multiple things in a larger general area that a healthy person may look at and it may vary which they look at first. Similarly there may be multiple things that persons at various levels of the condition will look at. Thus, because these scene elements have meanings, a cluster of POI responses (seen in FIG. 9A as dots) will be tighter (more densely packed than the meaningless frames just discussed that will normatively be discarded). In these cases, it is not only unavoidable but beneficial to have multiple confinement areas for scoring even if they overlap as will be seen.

It should be repeated that, despite the examples given, the values for the target full value radius and the algorithms in any selected spatially depreciating response curve can be implementer-selected by any means including prior implementer experience (with subjectivity dealt with in subsequent optional optimization). In examples like the one just discussed where the single negative target full value radius was driven by the standard deviation of the full distribution (for example, when performing this process on the first group, i.e. healthy subjects, the full distribution is all POI's captured from healthy subjects for that frame which should be the number of healthy subjects, 100 in this example), it was appropriate to divide the portion of that 100 associated with a Gaussian distribution by one since there was only one negative confinement area (with an 804). This is why, in the above example calculations, we set T to equal one.

However, when there are multiple negative or multiple positive clusters of significant (e.g., statistically dense enough to represent a tendency rather than random action) POI's (dots), implementers might presume that each of the individual confinement areas like 804 would represent Gaussian distributions of subsets of the total population. This is one of the reasons that 100 (used in an example here as the total population of healthy subjects solely because it is easier to explain with percentages) is a placeholder for an ideally larger number. If the T confinement areas share essentially equal POI hits for the instant frame, the above logic of dividing by T is useful. Otherwise, implementers can apply weighting as appropriate.

This implementer-directed process is intuitively satisfying, favors apprehension of error, and will be preferred by implementers preferring a hands-on, didactic process particularly while learning the nature of responses to a given video and/or for a given group of subjects with known conditions. The steps of automation of many or all of these key processes is understood by those skilled in programming, statistics, graphics, and imaging. Further, Approach B, described below, provides substantial additional and applicable programming information applicable to any desired automation of this Approach A.

Approach B for PCR:

There can be many frames in a video resulting in much work in PCR and, with that tedious work, opportunities for error. An alternative approach to performing step two of PCR (including anchor finding), described now, can be less subjective and more automated. Towards this end, there are statistical packages available whose extensive functions identify clusters of points and the statistical nature of those clusters along with other features applicable to the PCR process of the current invention. However, while applicable to the current invention, they tend to be too long in both programmatic code and in functional description to be easily included in the text of this specification. While these applicable packages may be used to fulfill at least some of the PCR process, a brief alternative example approach will now be summarized. It will be best understood when recalling that our goal is the same goal we had for Approach A, that is to identify and value the clusters of POI's (that is, the anchors seen both in the circles of FIG. 9A and the data in database files like ScoringChild) for each frame. Like Approach A, once the areas are identified and at least approximately valued, they may be optionally and subsequently optimized.

As in the example description for Approach A above, we will sometimes describe performing PCR on only one group (e.g., healthy subjects suggesting negative scores) realizing that the described operations must also be performed on the other groups in order to have a scoring system representative of them. However, although not the preferred embodiment, PCR may be performed on any individual group to identify and value confinement areas and later be used on the general population to at least screen for the characteristics of that potentially singular group or of a smaller subset of all groups. Thus, a minimized embodiment of the current invention might gather data from only one condition group and then use the magnitude of scores based only on anchors for that condition as an indication of the instant reviewer's degree of symptomatic affiliation with that group.

Figure 9B:
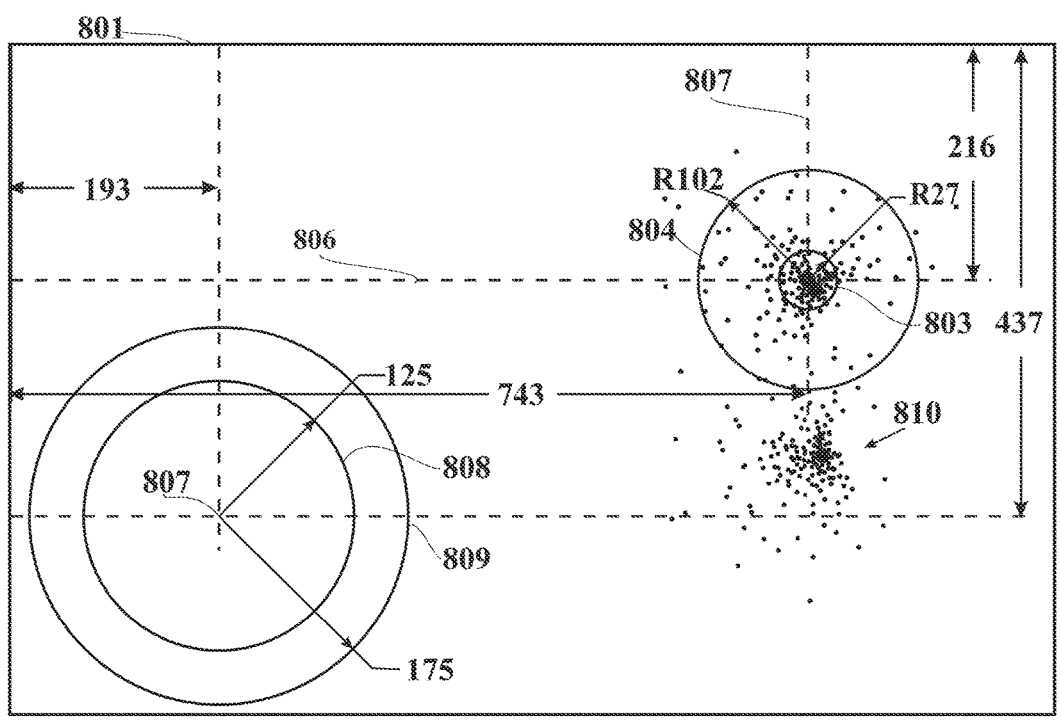

Location and Calculation of Target Full Value Radii and Spatially Depreciating Response Curves:

Let's consider FIG. 9B without benefit of the circles 803, 804, 808, and 809. In other words, we see the dots but we haven't yet figured out where the confined areas should be located based on cluster scattering and there are no humans to look at a scatter map and visibly recognize the centers of or the separations between such confinement areas There are many applicable approaches to identifying the centers and locations of clusters including the application of well-known statistical principles including calculating root mean squares of POI locations that are progressively further from a point in the image being considered. There are many such approaches that will certainly be used as part of the current invention by implementers. To describe a preferred embodiment, an alternative and simple, yet tunable, approach will be described here.

To communicate somewhat complex ideas, we will use herein, in addition to textual descriptions, program code snippets that are not necessarily specific to any particular programming language and are not intended to be operable in their current form in any particular language or under any particular operating system but will be easily understood from the level of detail provided by most anyone skilled in the field of computer programming.

Recall that we come here with all of the POI data in the data structure of FIG. 7D which is useful for the work associated with the capture and maintenance of captured data. However, in the data that will be used in this step, subject number is not needed or desired both for data efficiency and to enable maximum (and often Independent Review Board, IRB, required) separation between subject private information and potentially publishable clinical data. Thus, we now produce a single table from the table of FIG. 7D containing, for every POI captured, only frame number, subject condition, and target coordinates indexed by frame number+subject condition. This table can be stored in any format and reused. For speed of processing, these data may be placed in the one-dimensional arrays:

1. frame ( ), condition( ), and POI( ).

where the suffixes of each of these arrays recall the order of the target coordinates and the associated frame and condition data. Thus, if there were 100 healthy subjects (with subject condition #1) the value stored for frame(1)=1, condition (1)=1, and POI(1) is equal to the POI location of a healthy subject when watching frame number 1. The value stored in frame (101) would still be=1 (we're still in the first frame) but the value for condition (101) would be=2 and the value for target (101) is the POI of a subject watching frame number 1, etc. Thus, the array is ideally placed in an order that can be scanned with an incrementing suffix to rapidly consider, through each frame number and subject condition, all of the POI's that occurred in a frame for subjects of that condition. Exemplary use of this preferred array structure is in the programmatic descriptions of FIGS. 11-13. Where IRB required, the initial capture of this data may be put directly into this array format in the first place maintaining the desired order but removing any subject information reference.

Example Token Code:

The general and partial code segments shown in FIG. 11 are merely illustrative of the basic approach. They also use names longer than many naming conventions actually permit to better convey more clearly what values are. Further below many of the programmatic steps will be described in a narrative. These programs pick up in FIG. 11 after the captured POI data whose capture was described above is transferred to the first set of global arrays described above (condition( ), frame( ), and POI( ).

No particular screen resolution is inherent in the implementer already-established variables for)(Range and YRange indicative of the pixels of rows and columns respectively in the implementer's screen hardware. Also, some high resolution screens may provide more spatial resolution than eye tracking equipment may be able to match and processing speed slows when extremely dense matrices of many pixels are used. Where that is the case, implementers may choose applicable embodiments where every pixel location will not be considered as they are in the code snippets we discuss here. For example, for a very high resolution giant screen somewhat distant from the viewer, it would not be unreasonable for implementers to use, for example, only every $10^{th}$ or $15^{th}$ pixel location laterally and vertically in a sparser matrix as is easily performed by those skilled in the art and then match eye-tracking captured locations to the nearest available thus-selected points on those sparser matrices. In many applications this can be done to substantially accelerate processing and minimize data storage overhead. It will also substantially increase optimization calculation.

The steps already described above can provide usable data without need of further optimization. However, the structure and process of the current invention allow it to thrive on even very large population samples of subjects enabling more accuracy and, additionally, a potential for discovering condition signatures in the data that would be overlooked by humans awash in a flood of seemingly random artifacts.

Also, optimizations may optionally be at the frame level. That is, each frame can be optimized by all of the POI data for all subjects of all known conditions viewing the video. This is, in fact, the first option explained in FIG. 11.

Alternatively, a singular set of optimization criteria can be obtained with automated optimization and used for all the frames of an entire video or multiple videos.

Very Brief Narrative of the Code Snippets:

A very brief overview of the provided code segments beginning with FIG. 11 is now provided and will be followed by more detailed discussion of key points.

FIG. 11 begins with a typical setting of global (or public) variables and default values.

Then the as yet empty database ScoringChild is opened and indexed as the future container for scoring anchors soon to be identified. The other table, opened next, is for the later storage of SPT anchor scoring parameters and a measure (the field "Score") of how well those parameters resulted in the recognition of a particular condition level and, additionally, how well these condition levels were distinguished from each other (i.e., how well POI scores from a person of one condition was kept from affecting the scores for another condition thus helping to prevent false positives).

Next, the program GrandTour( ) is called which begins in FIG. 12A. It begins by iteratively testing a very wide range of parameters that are used in the identification, location, and valuing of scoring anchors (e.g., DefRange1, DefRange2, DefRange3, and MinHits and potentially many others that are not illustrated in this already not-so-brief example).

For each of the iteratively attempted combinations of these calculation factors, the program MakeAnchors is called (seen in the lower half of FIG. 12A and completed in FIG. 12B). Using the instant set of these parameters to be tested, MakeAnchors creates a complete set of scoring anchors applicable to scoring any later viewer being tested. It is also selective in that it does not create anchor records for areas of little POI concentration. This program also answers the question "what kind of code can be used to turn raw subject data into scoring anchor templates" since that is precisely what it does.

However, this is the grand tour of all the possible iterations of the very parameters that determine the size of the areas determined to be indicative of a condition, how their density or power is to be distributed spatially, the valuation of a POI location at any point, and which image locations should simply be ignored when a POI is there. Thus, the purpose of MakeAnchors in this unusual application is to make all the anchors for one iteration set of parameters and then score all the POI data we have on all subjects of known conditions with these custom created anchors and then determine if that is good data. If it is good data, then these are good parameters.

To do this, as soon as MakeAnchors returns to the deeply nested iterative loops at the top of FIG. 12A, the program ScoreVictims is called. Some might call this program "ScorePatients" but those people are not writing a patent specification at 2 AM.

ScoreVictims, in FIG. 10 self re-curses to run three sets of calculations.

The first time through ScoreVictims, it simply applies the POI locations, captured earlier into an array, to those scoring anchors from the table ScoringChild to get the scores. For the four condition types used in this example, each POI is only applied to the condition type of the person who's POI we are scoring the impact of.

In the second pass through ScoreVictims all calculations are based on the POI's for subjects at one condition level being applied for scoring to the scoring anchors for the next lower condition group (a leftward shift comparison). For example, a POI for condition number two is running against the scoring anchors that were developed using the POI's for condition number one. When we begin testing with subjects of unknown condition, we will not want a person whose real condition is condition number two getting scores from anchors associated with completely healthy users. This is a leftward shift calculation and will be used to see how well the instant parameters being tested in the grand tour calculate scoring anchors that prevent false positives by making the anchors for one condition level less sensitive to POI's from someone having a different condition level.

Similarly, in the third pass through, a rightward shift comparison results in, for example, a POI from condition number one being too sensitive to the scoring anchors developed for condition number two.

Upon completion of the third pass, and in the middle of FIG. 10B, a single numerical score on 10 different measures of those comparisons is made using implementer-adjustable levels of standard. A perfect score is a score of 10 which means that, in addition to the low-density anchor prevention of MakeAnchors, ScoreVictims verifies that each condition has sufficient hit magnitudes and that for each condition level there is separation from the next lower and next higher level conditions to reduce bleed-over and false positives.

Thus, the optimization, in addition to verifying proper and substantial magnitude of "hits" within a condition type, selects combinations of parameters that best prevent viewers with one condition from scoring highly on scoring anchors that are based on subjects with other condition levels (only some of which are included in the OptimizationDataFBF table in FIG. 11).

Thus, FIGS. 11 through 13 illustrate subprograms for automatically and less subjectively creating potentially extensive scoring anchor templates (covering any amount of the image) directly from even extremely large POI datasets, automatically scoring POI's from both subjects with known conditions (for validation) and from subjects being diagnosed, and for optimizing the parameters that drive all of the above in a process based on actual end results from iterative testing of wide ranges of such parameters.

Finally, due to the capacity to handle very large numbers of combinations of even substantially disparate anchor areas that are ostensibly unrelated to a single condition and the potential to non-subjectively optimize these artifacts into groups of scoring templates, an enhanced ability to recognize and quantify less-obvious phenomena is possible.

More Discussion of Elements Described in the above Code Snippets:

Yet another form of optimization, additive to and typically subsequent to the optimizations just discussed, for additional fine-tuning, involves the selective flagging for deletion of selected scoring anchor records that were acquired earlier in the programs of FIGS. 11-13. In the preferred embodiment of this extra fine tuning optimization, the optimization values (obtained earlier by the GrandTour program and other programs shown in FIGS. 11-13 and stored in the table OptimizationDataFBF) are later used to iteratively score POI's as is done in the processes of FIGS. 11-13. However, in this last optional step, as the POI's of known subjects are iteratively scored, that scoring is done with a different scoring anchor missing in each iteration. It will be normative that this will tend to reduce rather than increase the score. However, applying the left shift right shift principles for grading shown in the ScoreVictims program, it may be found that the remaining scoring anchors and result in better separation between the condition levels. That additional iterative process will enable the sequential removal of anchors detrimental to good separation.

If the removal raises the magnitude of the score or increases its score distinction from other condition scores this anchor (e.g., the database table ScoringChild) record is marked to be ignored and will not be used for scoring in the future. This iterative process continues until every scoring template in every frame has been thus considered for separation from the scoring process while in the presence of all of the others.

Multiple Optional Scoring Strategies:

After the scoring templates have been developed from subjects with known conditions, a new subject to be diagnosed can have his POI's captured using the exact same capture process. However, there are several options available to implementers in how to use this POI data. For example, the single set of POI data can be run against each condition's anchor scoring data individually to see which obtains the highest magnitude score; the data group resulting in the largest score indicates the group most applicable to the instant subject.

Alternatively, since the condition one group has negative values for scoring anchors and the others have positive values, the subject being diagnosed may have his POI scored against all of the scoring anchors and summed and the net magnitude of the positive and negative values from applying his POI's is his score or a product component of one. Thus, if a person having positive characteristics does, in fact, look where a healthy person would look, it will and should reduce his positive score with the responsive negative score component.

In this embodiment, it will not be unusual, when properly optimized and/or optionally adjusted by implementers for better "channel separation" (the data discretion between the condition levels) for condition three scoring anchors to have higher values for target strike values than condition two scoring anchors, etc. Thus, in this embodiment, a severely affected subject would likely, in addition to scoring high in his own condition category, traverse the scoring anchor locations of lower condition scoring anchors as well. This will result in an appropriately much higher score for a much higher subject tendency in the direction of the condition being measured. Thus the magnitude of the score can be directly associated with the degree to which the subject is affected by the condition being diagnosed.

There will also be many other applicable variations on these themes including hybrids such as a concatenation of the scores for the two approaches just discussed.

Strabismus:

Research unassociated with the study of Strabismus has also established that there is a powerful cognitive and vision-system phenomenon known to aggressively facilitate conditions conducive to clear vision even when this requires brain-directed tasks that normally have nothing to do with vision perception. Thus, the brain appears to have a learning plasticity that enables it to recognize indicators of and causative agents for vision clarity and to orchestrate immediate responses favorable to clear vision. These factors and the effectiveness of the comparatively unpleasant current treatments suggest that applying deprived vision clarity as a response to instant failures of binocular synchronization is an effective means for treating Strabismus. When that deprived vision is delivered by the current invention, it also has the advantages that it can be applied early in the development of the vision system before the subject is verbal and can be tolerated for more extended periods with less supervision.

Thus, strabismus is another example of a condition recognizable and treatable by the current invention. As extensively described above and elsewhere herein, and following steps, some of which are outlined in FIG. 3 with programmatic support in FIGS. 11-13, subject POI's are captured in any of the viewing scenarios discussed herein as the viewer watches.

The operations for dealing with strabismus can follow the same detailed steps outlined in FIG. 3. However, for strabismus, step D (disorder/normative scoring) in FIG. 3 can be simpler than, for example, autism. Many eye-tracking systems, including ones like 108 in FIG. 1, provide, to a personal computer (like 109 which can run the control software) coordinate values relative to POI screen positions on the display being viewed. Thus, the location on the screen being viewed is easily known by simple scream position data. Some also calculate and provide a representative vector of each eye's vision axis and even the distance from a point between the viewer's eyes to the intersection of the viewer's vision axes and thus providing the distance to the viewer's point of focus.

Condition Recognition Factors: By Distance to Vision Axis Intersection

Figure 2:
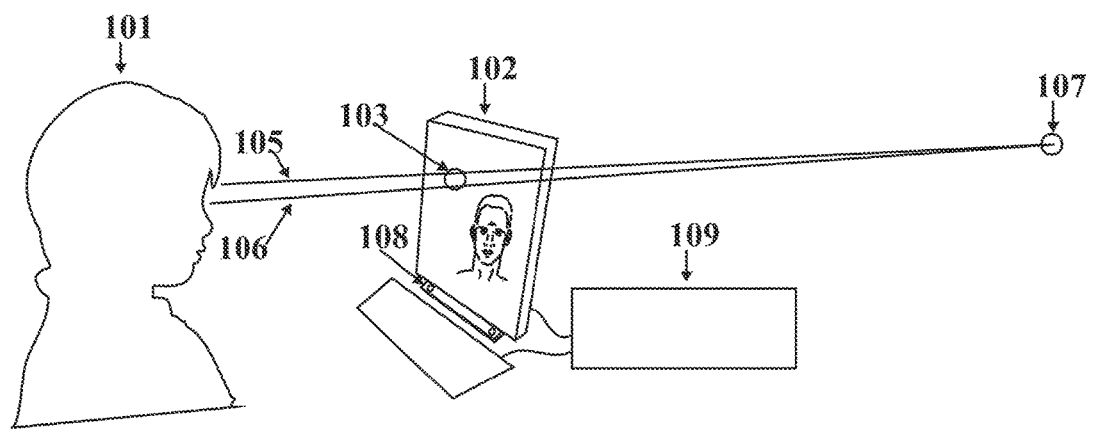
FIG. 2 is the assembly of FIG. 1 wherein the convergence of the observer's eyes occurs at a point, 107, distal to the screen, 102.

At this point, one of the most pleasingly easy to use embodiments of the current invention is discussed. A subject, such as the young 101 in FIG. 1, viewing a monitor 102 with POI at 103 being observed by the eye-tracking assembly 108 with results being captured by the control software running on computer 109. In FIG. 2 it can be seen that his actual focus is behind the screen possibly because one eye has wandered away from a closer intersection with the visual axis of the other. The subject is seated at a known distance from the monitor. The control software either accepts the vergence-based distance from the viewer 101 to the intersection of his vision axes that is provided by the eye-tracking assembly or calculates that same distance to the user's point of focus (POF) by very well understood trigonometry based on the angle of eye axes vectors provided by the eye-tracking assembly. Either way, that distance can simply be subtracted from the known distance between the viewer and monitor as a surprisingly useful indicator for degree of strabismus.

Although this seems to be the simplest embodiment possible, it was found to be unusually effective. As the lazy eye dysfunctionally moves even slightly away from a normal vergence with the strong eye, a substantial disparity rapidly emerges between the a priori distance between subject and monitor and the distance to their current point of convergence. This is eminently recognizable by the difference between the a priori distance and the distance provided by the eye-tracking assembly (or where unavailable the control software calculated distance to eye axes intersection). Thus it was found effective to simply set up a range of corrective stimulation responses based on distance.

Based on the now-known millimeters (mm) of "error" between the known distance to the monitor and the calculated range, a graduated level of Gaussian blur was applied responsive to the magnitude of that error. That graduated response was managed with five tiers based on the mm of error. The first tier was 150 mm. if the error was less than 150 mm, no corrective stimulation was applied.

If the difference between the a priori distance and that calculated was less than 150 mm, no defocus was applied. If the difference was between 150 mm and 175 mm Similarly, for differences of 176-200 mm, 201-250 mm, and >250 mm, levels of defocus were increased until in the last group the image was effectively imperceptible (nearly completely defocus).

Corrective Stimulation:

This embodiment is also exceptionally easy to provide at least some modicum of corrective stimulation without writing a lot of software. For example, when the computer 109 is displaying the image with a QuickTime-based video player, the video may be blurred to a desired degree by applying a Gaussian filter to every frame using, for example, Apple's Core Video technology for blurring me QuickTime-based video image.

Thus, by simply having the control software operating on 109 call a commercial program to blur the image being displayed relative to the numerical magnitude of a past variable, the viewer's image was continuously responsive to the viewer's binocular fidelity.

As the lazy eye begins to move away, the distance calculation exposes both the presence of binocular infidelity and a measure of its magnitude. A measure of this magnitude is used to determine the degree of responsive blurring. Then, as the lazy eye returns to normal vergence with the strong eye responsive to the inability to see the image, the distance error decreases as does the degree of corrective stimulation. This provides an immediately apprehended perception by the viewer of a cause and effect relationship between binocular infidelity (when the two eyes just can't stay together at a mutual POI) and the inability to see the video which is evocative of fusional vergence.

Other Recognition Factors of Binocular Fidelity and other Indications for a Positive Score:

There are a number of additive and/or alternative methods for rapidly recognizing the presence of binocular infidelity. Incorporating these indications along with (in addition to) the above process can improve performance and provide useful checks and balances. There is certainly no advantage in a false positive and compliance is inversely proportional to the number of frustrating false positives. Thus, in an additional embodiment, multiple factors are used to recognize binocular infidelity.

Eye elevation, observing one eye at a different relative cyclopic elevation than the other is an indicator of binocular infidelity. That is because, as is well known in Ophthalmology, the two eyes normally track together in some transverse plane. That is, the elevation of the left eye is normally the same as that of the right eye with respect to the cyclopic origin (which moves with the head). One benefit of this option (which is based on dysfunctional disparities in eye-elevation) is that it requires no known distance to POI information. Another is that it is additive to the other indicators for faster and potentially broader sensing of dysfunction. Also, is applicable to worn eye-tracking assemblies like FIG. 5.

Inactive/active partners: When one eye moves and the other does not, this is an indication of dysfunction.

Strong-eye leadership: It is typically already known which eye is the strong eye and which is the weak. Based on this knowledge, it is an indicator of dysfunction when the strong eye begins or continues a path that is or becomes incongruent with that of the weak eye. For example, if the strong eye follows a path divergent to that of the weak eye (increasing inter-pupilary distance or IPD) that may simply indicate a more distal instant POI. However, if the strong eye continues its direction and the weak eye's changes, this is an indication of dysfunction.

Strong Eye Recognition:

It is normative for the strong eye to be an enduring condition. The current invention can recognize and indicate the strong eye.

The Eye that Best Follows Action:

As the current invention receives the eye tracking information responsive to images on the screen, for example in step C of FIG. 3, it can be used to both identify the strong eye and approximate the instant degrees of failure in mechanical fusional vergence (angle of squint). By very briefly placing an interruptive and discrete element on the screen (e.g., a brightly colored dot on a temporarily otherwise uninteresting background), the vision axis of the strong eye, as measured by the eye tracking equipment, will fixate upon and, when the locationally discrete element moves, follow the discrete element better than the weak eye. Thus, in addition to other diagnostic functions of the control software, the option to identify the strong eye with the placement of a series of interruptive points or images on the screen followed by comparison of which eye, as reported by the eye-tracking assembly, best fixates at that point, is disclosed.

Games that Train and Measure:

Single Image; Requires No Eye-separating Display

There are also other training and measurement games that do not require eye-separating display.

One Ball Games:

Here, after the strong eye is identified as described elsewhere herein, a game background image is displayed on the screen and a single ball is located at the intersection of the weak eye's vision axis and the screen. (The location of the point of each eye's vision axis intersection with the screen is a common feature in eye-tracking components and the overlay of an image at any given screen location over another image is so widely understood that it is not recapitulated here.) The game (or in other applications the job such as moving a cursor over an icon on the computer's main screen to execute a program) requires the viewer to move the potentially lazy eye so that its vision axis intersects the screen where he wants the ball to go. Analogous to exercises where the strong eye is paralyzed or covered, this process, by directing the action on the screen only responsive to the lazy eye, forces it to perform in exercises that can be highly geometric and as precise or flexible as desired by implementers.

Figure 4A:
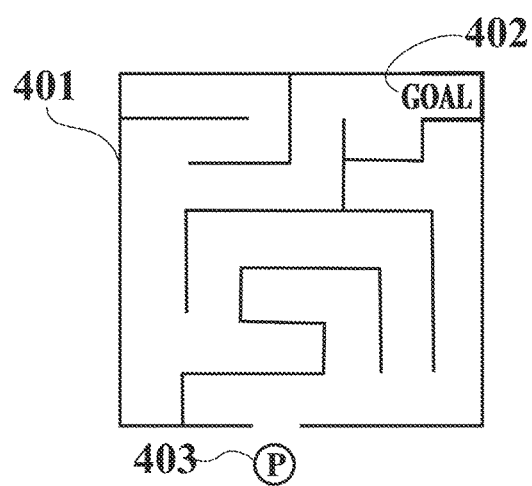
FIG. 4A and FIG. 4B support the verbal illustration herein of a path-finding game comprising at least a maze, 401 and a goal 402.
Figure 4B:
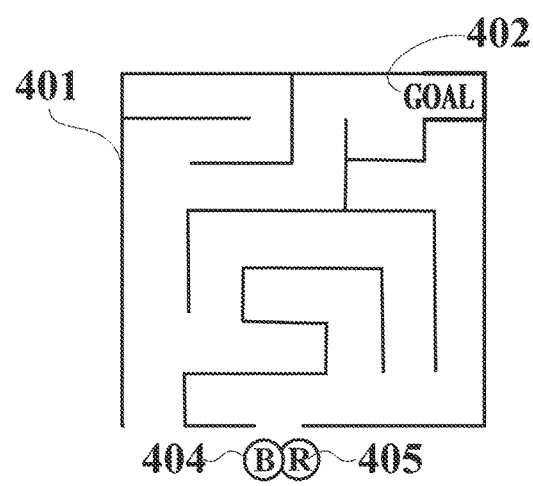

Twin Balls:

The "twin balls" training and measurement game tracks each eye and, responsive to the intersection of each eye's vision axis with the screen, locates a ball, icon, or other visual object at said points of intersection on the screen. Thus, a healthy viewer with normal correspondence will see the two balls (or other visual object which are presumed when "two balls" are mentioned) superimposed. One particular example is illustrated in FIG. 4A. A game background for one such as a maze fills most of the screen. A goal of any kind is located at 402 and a single purple ball 403 is positioned to enter the maze and it stays there for a few seconds. Then the ball slowly separates in FIG. 4B into a blue ball 404 and a red ball 405 with the overlapping areas of the two still remaining purple as the separation occurs to communicate the relationship between the balls. At this point, the blue ball is fixed but the red ball now moves to and continues to track with the point of the intersection of the lazy eye with the screen. If the actual intersection of the lazy eye's vision axis with the plane of the screen is so far off that it is outside the display perimeter of the screen, and arrow, not shown in FIG. 4, is displayed whose tip points to the location and whose tail points to the blue ball waiting at the entrance. The tip is preferably near the point on the screen periphery that an extension of the arrow would cross and the length of the tail is proportionate to the distance between the blue ball and the point of intersection of the vision axis of the lazy eye on the plane of the screen (indicative of the magnitude of the desired correction stimulus).

As the viewer moves the lazy eye, the red ball 405 (in this example) the game control software, responsive to the eye-tracking data for the eye previously identified as the lazy eye, moves the red ball on the screen in the direction of this change until it is close enough, within a tolerance, to the position on the screen of the blue ball 404. If the two balls are within an implementer-chosen tolerance of spatial coincidence, they become a single purple ball, if they merely overlap, the overlapping portion becomes purple. If the two balls are combined or are balls are combined or are at least close enough together to fit through the entrance of the maze, the location of the blue ball on the screen is then driven by the game-control software to now be located at the instant intersection of the strong eye's vision access and the screen, thus allowing the viewer to direct with his eyes the progress in the maze. Of course, in this example, the balls are not allowed to cross a line (using well established software techniques for virtual-object path control through virtual boundary borders which are not recapitulated here).

If, during that progress, the two balls separate far enough apart that they are no longer able to fit together through a channel in the maze, the ball responsive to the position of the strong eye stays where it is and temporarily ceases to be responsive to positioning of the strong eye until the lazy eye, still guiding its ball, returns that ball back to where it is close enough to the now-fixed strong-eye's ball to fit through the maze. The game control software, when that condition is achieved, reactivates the relationship between the strong eye and the movement of its ball as it allows new progress for the two through the paths, based on implementer-chosen parameters for adequacy of closeness of the two balls for passage between the channels.

The maximum and average disparities between the positions of the two balls as well as the time required to progress the maze are parameters applicable to diagnosis of the condition's magnitude as well as enabling the benchmarking of progress over the period of rehabilitation. Also, unlike many of the quasi-static and slower response measures, approaches such as these, particularly when timed, are of increased value both for the development of higher-speed visual performance skills, and the measurement for the capacity thereof.

Separated Images:

I Ball Through the Channel; Squint Angle Measurement:

An additional measure of vergence error in degrees can be used in embodiments where individual images are provided for each eye. These embodiments include any of the many approaches for providing separate images to separate eyes. These include but not are limited to color separated glasses (e.g., the old red and green 3-D glasses), polarization separated glasses, shutter glasses, eye-individualized heads-up displays and direct projection to individual eye display. In embodiments where eye-image separation is accomplished through the use of worn optics that block the view of, for example, monitor-located cameras, the eye-tracking cameras are ideally located in the glasses themselves. For example, in polarization or shutter glasses, e.g., 501 in FIG. 5, a tiny camera 502 for each eye 503 in the frame of the glasses is preferred. Thus, at once, the wearer sees selective images for each eye and the control software, which typically controls the display, also simultaneously tracks where each eye is looking responsive to said individual images.

Based on research of the past, it might seem logical to just project a centrally located cross on the video image (analogous to a Cartesian origin in the center of the screen) visible to one eye while simultaneously projecting a dot visible to the other eye and prompt the user to tell us the apparent location on the Cartesian axis through the keyboard or voice recognition. While this, of course, is applicable to both the assembly and the objectives of the current invention, there are other options provided by the current invention more applicable to less cooperative (particularly pre-verbal viewers) and less patient (e.g., teenage) viewers. As is explained elsewhere herein, the numbers and magnitude of strabismic dysfunction can be identified and approximately measured by the current invention by other methods discussed herein (including the measurement of eye-tracking vergence errors indicative of a distance other than the known distance between the viewer and the screen as well as non-orthophoric degrees and even directions of adjustment, etc.)

However, an additional measurement strategy provides options applicable to corrective training, more measurement accuracy, less subjectivity, and no requirement for verbal or keyboard skills. One such embodiment of the current invention provides a brightly colored "ball" (602 in FIG. 6) on the screen 601 visible to only one eye by any stereoscopic display approach preferred by implementers). In one game environment, the brightly colored ball 602 is at the bottom of the screen 601 and moves only left and right at the bottom of the screen as the strong eye (which is the eye that sees the ball) moves left and right. (The game software simply places the ball towards the bottom of the screen and moves it left or right so that its position on the screen laterally approximates where the strong eye's vision axis intersects with the screen.) Somewhere above the lateral track of the ball is the video image of a channel e.g., 603, target or other objective with an incentivized reward (which may simply be a musical tone and/or reward graphic indicating that access to the next video has been accomplished and will immediately follow). For first-time users and those requiring more direction, a demonstration video first illustrates the ball 602 moving left and right until it is perfectly aligned with the narrow opening to the channel (or other reward entry location) and then, after a brief delay, being moved into the channel followed by the reward, e.g., instant music, image, or other announcement and a very brief but entertaining video, This is repeated several times from several different starting points for the ball with the same result until the viewer sees the relationship between the ball position and a the reward. Then, the screen with the ball returns but this time the lateral position of the ball on the screen, visible only to (due to stereoscopic separation) one eye (in this example will use the strong eye), is determined by the strong eye's vision axis. The relationship between the motion of the ball and the azimuth of the eye is quickly apprehended by the viewer. The rest of the screen, i.e. typically everything but the ball (here only the boundary lines 604), is visible only to the other eye (here the weak or lazy eye).

Healthy viewers can quickly "get the ball rolling" to the desired lateral point easily by looking from the ball to where they want it to be. Thankfully, it is human nature, as we seek to "will" something to move, that we seek to move it with our eyes. However, strabismic viewers will have a problem. Even when the ball is precisely at the channel, it appears to the uncorrelated viewer to be off to one side relative, of course, to the degree of strabismic error (squint angle). It would be nice to know that angle and without requiring any viewer input.

Because the eye-training software that guides this process continually adjusts in real-time the lateral position of the ball on the screen responsive to the calculated lateral point where the strong eye's vision access intersects the screen, as the viewer looks in the direction he wants the ball to go, the ball actually does move in that direction and, in doing so, also moves with respect to the actual screen location of the channel (using channel herein to represent any game target, etc.). When the ball stops and hesitates awaiting the reward, because in the adjusted binocular perception of the viewer the ball is at the target location, the difference between the location of the strong eye's current vision access intersection with the screen and the actual channel location on the screen is one measure of strabismus angle during an action sequence. (The mathematics of calculating this angle subtended between the two points based on the distance from the user's eyes to points on the screen, being well-known to all of those skilled in the art, is not detailed here.) Because the viewer is trained to anticipate a delay between the proper centering on the ball 602 (below the channel) and the incentive reward, the lateral distance on the screen between the paused ball and the actual lateral center of the channel (not as seen by the lazy eye but as actually presented on the screen) can provide a valuable measure of strabismus in a less quasi-static environment and without depending on data from verbal and/or subjective viewer impressions and responses.

Initially, the game-playing viewer is given substantial tolerance so that the reward can be obtained for positive reinforcement. However, using the game as a training mechanism for learned remediation, that tolerance can be gradually reduced over time proportional to any improvements over time to strabismus angle.

One example of an alternative vertical vergence measurement would be the horizontal training game just described rotated 90° as shown in FIG. 6B (where, for example, the ball stays at the left of the screen 601 and initially moves only up and down, and only enters the incentive channel 603 to the right, leading to the next video or other reward, when the ball 602 is at the level of the opening to the channel).

In both of the previous examples the views to each eye can be reversed in separate tests so that the weak eye determines the location of the balls 602 as they are displayed on the screen and the strong eye sees the channel. By doing this both ways we both provide data on each eye's performance as well as capture data for both angle and direction of strabismus.

Strabismus and Autism Simultaneous Application:

Because the elements of the current invention are applicable even to the very young and because both strabismus and autism emerge so early and both require early response, it is advantageous that the current invention can be used to both diagnose and treat both at the same time.

In a preferred embodiment for one such application, the viewer watches either a prescreened and coded or real-time coded (e.g., any movie or television program) video. For each frame, the viewer's eye-tracked eye positions are considered both for their motor correspondence and for POI's having autistic values.

When the viewer's POI strikes a positively-coded screen area (for convenience, herein "positively coded" means a score indicative of the dysfunction being tested for), diagnostic autistic scores are captured and tabulated as described elsewhere herein for later or real-time reporting on the presence, types, and magnitudes of autistic signatures. As in autism-only embodiments, the controlling software, by implementer control and/or user selection, can additionally apply remediative action. These actions may be chosen to be a blurring of the image relative to the magnitude of the positive score, vignetted highlight of preferred-focus areas, software-emulated diplopia, as well as any other sound or visible cues including the few that are discussed herein. However, in one preferred embodiment for combined autism and strabismus diagnosis and remediation, software-emulated diplopia is not used as a remediation stimulation for autism so that it can be used for remediation of strabismus. This allows the potential plurality of conditions being remediated simultaneously to have independently recognizable stimulation cues. As in isolated autism remediation (when strabismus is not being considered), magnitude of the autism remediation stimulation cues are reduced proportionately as the viewer's score becomes less positive (for example, when his eyes come closer to engaging a negative target such as adult human eyes or other locations as determined by implementers).

When the viewer's eyes, based on the numerous indicators for strabismus described herein and others that logically follow, indicate strabismic behavior, any of the stimulation cues may be implementer-chosen to prompt for remediation. While any of the cues may be used in any combinations, they should be selected by implementers to be independently recognizable.

For example, in one embodiment, the stimulation cues for remediation of strabismus is diplopia (that is, causing the presented image to be overlapping images spatially separated from each other to look like diplopia where the degree of that apparent binocular mis-registration is responsive to the degree of the strabismic behavior). The simultaneous prompt for correction of for autistic behavior can be vignetting. Here, the center of the vignetting effect can be the screen location of where implementers want the subject to be looking.

In programmatic terms, the display location where implementers want the subject to be looking may be as simply described as the TargetCoordinates value (a data field described herein) of the negative scoring anchor with the highest magnitude for the instant frame. Thus, when the instant POI's are being scored against scoring anchors (e.g., in step D of FIG. 3) and a highly positive score for autism occurs, the software selects from the sorted scoring anchor table (e.g. the ScoringChild example in FIG. 11) the record with the highest negative value for TargetStrikeValue and places the center of the vignetting at the screen location indicated by the value of TargetCoordinates in that same record.

Once the general programmatic basis for a single-malady diagnosis and remediation, discussed at length herein, is understood, programming for calculating both during the execution of a frame will be understood by those experienced in the field of programming. This is useful where multi-malady diagnosis is desired such as with small children watching television. Those familiar with computer programming understand how to make a sequential process look simultaneous by sequential processing and will also understand how this can be accomplished using the anchor scoring table (e.g., ScoringChild) to score POI's against scoring anchors for recognizing autistic traits while, sequentially but during the same frame, considering and quantifying strabismic cues (as described above) from instant eye-tracking data. Then, in step E of FIG. 3, the image can, for example, both be vignetted (responses to any autistic traits recognized) and made to appear more diplopic (responsive to any recognized binocular infidelity).

Having said all that and having illustrated what is the inventor's preferred embodiment for multiple malady diagnosis and remediation, it should be noted that there are many applicable alternative programming methods and remediation cues that can be equally effective.

When vignetting is thus used, the periphery of the image around the point the subject should be looking typically gets darker and the visible image in middle becomes smaller with both relative to the magnitude of the autistic behavior. When used as a cue for redirection in autism, this is to direct the autistic subject's eyes to the preferred location intuitively while preventing this direction from being mistaken as a correction cue for strabismus. Stimulation cues should be chosen to be intuitive.

Thus, it is actually possible to diagnose autism, strabismus, and other conditions simultaneously. It is also possible, where desirable, to treat them simultaneously. The viewer's eyes are drawn to the preferred attention area respective to autism while simultaneously requiring proper motor correspondence to see a sharp image.

Head-worn Eyetracking

For head-worn eye-tracking devices, after an initial calibration so the cameras know where the eye and/or eye-reflection landmarks are in the camera view, 3.4. Strabismic Display Imaging (SDI):

Emmetropic glasses, as detailed below in 3.5.1, have the potential for creating a defocus condition in the presence of binocular infidelity.

For non-presbyopic strabismics with otherwise healthy eyesight, however, the automatic defocus of emmetropic glasses as applied to strabismus requires further design constraints. The accommodative capacity of the otherwise healthy strabismic requires no correction. Thus, there is no focus correction applied responsive to a change in calculated distance. In other words, in the presence of substantive natural accommodation there is no need for the distance-driven external accommodation (that conveniently provides defocus responsive to binocular infidelity).

Since this does not affect the SDI approach used in this research (SDI is not affected by this since its defocus is screen-driven) and thus has no evaluation in the current research, it is covered here only very briefly. Future research will determine which methods are the most effective for the emmetropic glasses embodiment.

A variety of processes may be used to narrow the DOF of the subject and move the center of that band with respect to the calculated POI. E.g., for a subject requiring no focal correction, the emmetropic optics themselves may be directed to offset sensed and/or calculated/predicted eye lens diopters to artificially offset accommodation. Alternatively, the accommodative capacity may be limited in a distance driven manner by effecting, with the optics of the emmetropic glasses (which are passive in the absence of binocular infidelity) a degree of myopia or hyperopia that places the calculated POI (based on actual eye-vector intersection) in focus. If, however, the true POI is not at the point of intersection of two vision axes (binocular infidelity), a defocused condition results.

Additively, the distance-independent vector indicators in 3.5 can be used independently and may also be used in coordination with the above processes to ensure a richer, more sensitive system.

3.5.2. SDI Management of Binocular Fidelity:

SDI's indication of dysfunction is, perhaps, more easily understood than the emmetropic model. Also, the list of distance-independent indicators in 3.5.1 is also applicable to SDI. SDI determines Strabismic dysfunction from a priori monitor distance related to calculated POI range. Thus, binocular fidelity is currently scaled by the difference between the actual distance to the monitor and the distance indicated by the intersection of the two vision axes, which is itself driven by the two eyes' azimuths.

Also, in future research the distance to the monitor itself will be corrected by the ranging system's ranging data averaged over time with anomalies above a threshold removed. It is believed that most subjects' eyes will behave enough to estimate the true current distance to the monitor over time. However, in all of our very preliminary testing to date, we have simply compared calculated POI range with an approximate known distance to the monitor.

This desirable state (appropriate focus support) is effected by an electro-optically varied focus in the lenses of the emmetropic glasses to be added after the initial ranging portion of the research is complete. (Other dynamic correction mechanisms are, of course, applicable but electro-optics are used here as an example embodiment.) However, in the presence of Strabismic dysfunction, one eye's departure from the other eye's POI will result in a different (normally very different as one eye wanders off) intersection of the two vision axes of the two eyes. If, for example, the subject is talking with someone nearby (fixating on their eyes) and the right eye then detaches from the POI (e.g., pans to the right in a normatively significant degree), the intersection of those two vision axes will move from a couple of feet to well behind the true POI. As a result, the natural emmetropic process will demand a lens diopter setting for a distance distal to the POI resulting in defocus. Only by returning the lazy eye to binocular synchronization can the brain regain clear vision through a now-corrected emmetropic optic.

What is claimed is:

1. A device for a viewer comprising:
   a display;
   an image to be displayed on said display to the viewer;
   an eye-tracking assembly;
   a processor;
   an image degrading element; and
   a memory configured to contain programmatic code that, when executed by said processor in coordination with the output of said eye-tracking assembly, is configured to direct the image degrading element to degrade at least one part of said image responsive to the user looking at a location with respect to a recognizable element in the image associated with an unhealthy behavior and, responsive to the viewer subsequently looking at a location that is at least less associated with an unhealthy behavior, to at least degrade the image less.

2. The device of claim 1, wherein the operations that result from the execution of said software on said processor further comprise:
   calculate a value based on where the user looks with respect to the location of said recognizable element wherein
   said value is at least indicative of any presence of a said unhealthy behavior.

3. The device of claim 2, further comprising:
   a sound component producing, responsive to said value, sounds chosen from the group:
   a sound associated with being unhealthy;
   a sound associated with being healthy;
   a sound indicative of the magnitude of said value;
   a verbal message responsive to said value.

4. The device of claim 2, wherein
   said value is based at least on criteria chosen from the group:
   the proximity of where said user looked to the location of said recognizable element,
   a known measure for how much those with an unhealthy behavior condition tend look where said user is looking,
   a known measure for how much those with a healthy behavior condition tend to look where said user is looking, a determined measure at least indicative of how much a look at where said user is looking affects said value; and wherein
said image degrading element is one of
1) a separate hardware device associated with said processor and said display,
2) a part of said programmatic code or
3) a combination of 1 and 2.

5. The device of claim 1; wherein
said image degrading element degrades at least one part of said image in a manner chosen from the group: dimming its display; simulating diplopia, modifying its apparent focus; effectively vignetting said image; modifying displayed color.

6. The device of claim 1, wherein
said processor communicates with said user with responses chosen from the group:
at least one displayed indicator on said display indicating a location where those practicing unhealthy behavior tend to look;
at least one displayed indicator on said display indicating a location where those with healthy behavior tend to look;
at least one displayed indicator on said display indicating where said viewer should look;
a reduction in the image visibility seen on at least parts of said display responsive to said user looking at a location with respect to said recognizable element known to represent unhealthy behavior.

7. The device of claim 2 wherein
said processor calculates a diagnostic score based on a plurality of said values calculated by said processor over time.

8. The device of claim 1, further comprising:
a video camera to provide said image; wherein
said device is able to compel a gaze direction continuously and in real time.

9. The device of claim 8, wherein
at least said display portion of said device is worn by the user; and
said display aligns said image with the normal view before said user; wherein
said user perceives objects in said image to be where they actually are.

10. The device of claim 1, wherein said image is a video image; wherein
the rapidly provided series of images enables the device to compel a user gaze direction in real time.

11. A method for correcting a user behavior comprising the steps of:
determining where, in the view of the user, the user is looking;
obtaining a scoring value based on what the user looks at;
compelling a user change in gaze behavior by automatically limiting in real time the clarity of at least part of what the user sees to a degree that is responsive to a said scoring value associated with unhealthy behavior; wherein
by making it more difficult for the user to see when looking at a location associated with unhealthy behavior, the user is compelled to modify behavior and, responsive to the user looking at a location associated with healthy behavior, lost clarity is automatically restored.

12. The method of claim 11 wherein
the steps of claim 11 are repeated beginning with the step of determining where, in the view of the user, the user is looking.

13. The method of claim 11 wherein
said scoring value based on what the user looks at is determined by where said user is looking with respect to the location of at least one recognizable element in said view.

14. The method of claim 11 wherein
the limiting of said clarity of at least part of what the user sees is effected by one of:
1) altering the transit of at least some light headed towards at least one eye of said user before it enters said eye or
2) limiting the displayed clarity of at least one part of a displayed image viewed by said user.

* * * * *